(12) United States Patent
Ditto et al.

(10) Patent No.: US 9,043,158 B1
(45) Date of Patent: May 26, 2015

(54) MORPHABLE LOGIC GATES USING LOGICAL STOCHASTIC RESONANCE IN AN ENGINEERED GENE NETWORK

(75) Inventors: William Lawrence Ditto, Kaneohe, HI (US); Adi R. Bulsara, San Diego, CA (US); Anna Dari, San Diego, CA (US); Behnam Kia, Honolulu, HI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 588 days.

(21) Appl. No.: 13/370,154

(22) Filed: Feb. 9, 2012

Related U.S. Application Data

(60) Provisional application No. 61/441,524, filed on Feb. 10, 2011.

(51) Int. Cl.
*G06N 3/12* (2006.01)
*G06F 19/12* (2011.01)

(52) U.S. Cl.
CPC ............ *G06N 3/123* (2013.01); *G06F 19/12* (2013.01)

(58) Field of Classification Search
CPC .......... G06F 19/12; G06N 3/002; G06N 3/12; G06N 3/123
See application file for complete search history.

(56) References Cited

U.S. PATENT DOCUMENTS

| | | | |
|---|---|---|---|
| 6,774,222 B1 * | 8/2004 | Schneider et al. | 435/69.1 |
| 7,924,059 B2 * | 4/2011 | Ditto et al. | 326/104 |
| 2006/0051838 A1 * | 3/2006 | Hwa et al. | 435/69.1 |

OTHER PUBLICATIONS

Dari, A., Kia, B., Bulsara, A. R. & Ditto, W. Creating morphable logic gates using logical stochastic resonance in an engineered gene network. Europhys. Lett. 93, 18001 (2011).*
Ando, H., Sinha, S., Storni, R. & Aihara, K. Synthetic gene networks as potential flexible parallel logic gates. Europhys. Lett. 93, 50001 (2011).*
Dari, A., Kia, B., Wang, X., Bulsara, A. R. & Ditto, W. Noise-aided computation within a synthetic gene network through morphable and robust logic gates. Phys. Rev. E 83, 41909 (2011).*
Hasty, J., Isaacs, F. J., Dolnik, M., McMillen, D. & Collins, J. J. Designer gene networks: Towards fundamental cellular control. Chaos 11, 207-220 (2001).*
Hasty, J., Pradines, J., Dolnik, M. & Collins, J. J. Noise-based switches and amplifiers for gene expression. Proc. Natl. Acad. Sci. USA 97, 2075-2080 (2000).*
Isaacs, F. J., Hasty, J., Cantor, C. R. & Collins, J. J. Prediction and measurement of an autoregulatory genetic module. Proc. Natl. Acad. Sci. USA 100, 7714-7719 (2003).*
Murali, K., Sinha, S., Ditto, W. & Bulsara, A. Reliable Logic Circuit Elements that Exploit Nonlinearity in the Presence of a Noise Floor. Phys. Rev. Lett. 102, 104101:1-4 (2009).*
Brandman, O., Ferrell, J. E., Li, R. & Meyer, T. Interlinked fast and slow positive feedback loops drive reliable cell decisions. Science 310, 496-498 (2005).*
Zhang, X.-P., Cheng, Z., Liu, F. & Wang, W. Linking fast and slow positive feedback loops creates an optimal bistable switch in cell signaling. Physical Review E 76, 031924 (2007).*
D. Gibson et al.; Creation of a Bacterial Cell Controlled by a Chemically Synthesized Genome; Jul. 2, 2010; vol. 329, Science, 52-56.

* cited by examiner

*Primary Examiner* — Soren Harward
(74) *Attorney, Agent, or Firm* — SPAWAR Systems Center Pacific; Kyle Eppele; J. Eric Anderson

(57) ABSTRACT

A method for providing a biological logic gate comprising the following steps: subjecting a bistable autoregulatory gene network (GRN) to a noisy background; identifying adjustable parameters of the GRN; using logical stochastic resonance to determine values of the GRN parameters which result in the GRN performing different logic gate functions; and setting the parameter values of the GRN such that the GRN performs a first logic gate function.

12 Claims, 17 Drawing Sheets

| AND gate | | |
|---|---|---|
| A | B | X |
| 0 | 0 | 0 |
| 0 | 1 | 0 |
| 1 | 0 | 0 |
| 1 | 1 | 1 |

*Fig. 3A*

| OR gate | | |
|---|---|---|
| A | B | X |
| 0 | 0 | 0 |
| 0 | 1 | 1 |
| 1 | 0 | 1 |
| 1 | 1 | 1 |

*Fig. 3B*

| NAND gate | | |
|---|---|---|
| A | B | X |
| 0 | 0 | 1 |
| 0 | 1 | 1 |
| 1 | 0 | 1 |
| 1 | 1 | 0 |

*Fig. 3C*

| NOR gate | | |
|---|---|---|
| A | B | X |
| 0 | 0 | 1 |
| 0 | 1 | 0 |
| 1 | 0 | 0 |
| 1 | 1 | 0 |

*Fig. 3D*

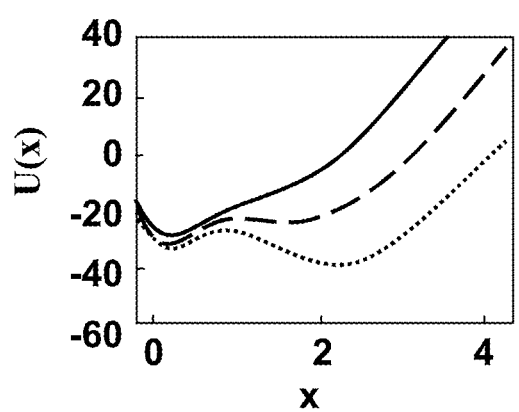 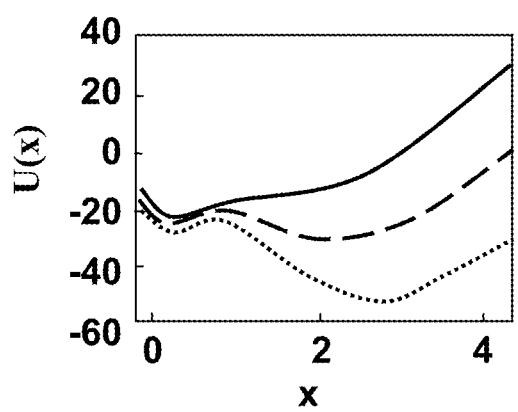
*Fig. 6A*　　*Fig. 6B*

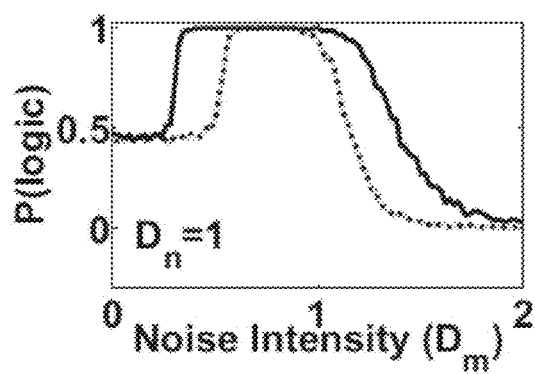 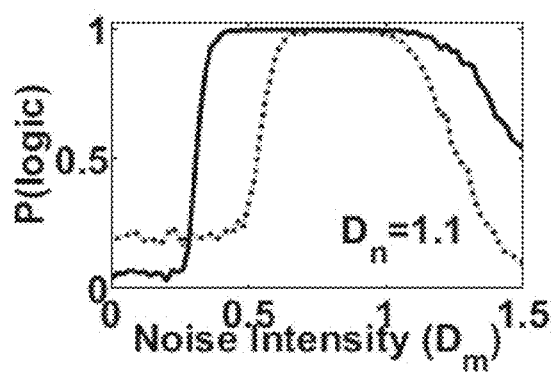
*Fig. 14A*　　　　　*Fig. 14B*

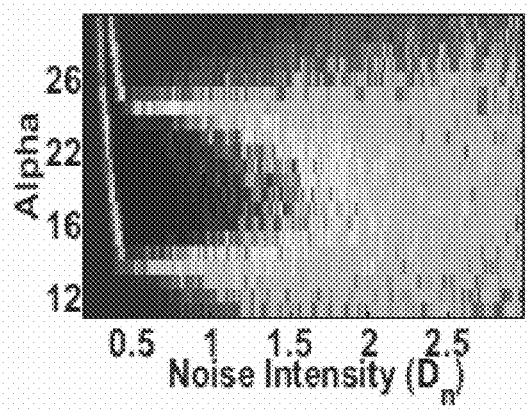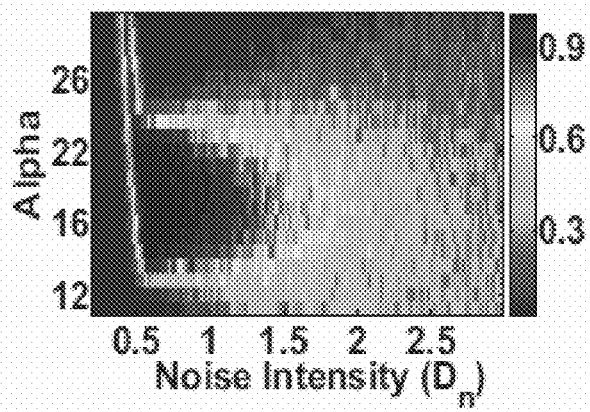
*Fig. 17A*  *Fig. 17B*

MORPHABLE LOGIC GATES USING LOGICAL STOCHASTIC RESONANCE IN AN ENGINEERED GENE NETWORK

CROSS-REFERENCE TO RELATED APPLICATION

This application claims the benefit of the filing date of U.S. Provisional Application Ser. No. 61/441,524, filed on 10 Feb. 2011, the disclosure of which is incorporated by reference herein in its entirety.

FEDERALLY-SPONSORED RESEARCH AND DEVELOPMENT

This invention is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-5118; ssc_pac_t2@navy.mil. Reference Navy Case Number 100728.

BACKGROUND OF THE INVENTION

An important goal for synthetic biology is to build robust and tunable genetic regulatory networks; these networks must be capable of performing assigned operations usually in the presence of noise.

SUMMARY

Disclosed herein is a method for providing a biological logic gate. The first step of the method provides for subjecting a bistable, autoregulatory gene network (GRN) to a noisy background. Next, adjustable parameters of the GRN are identified. Then, logical stochastic resonance is used to determine values of the GRN parameters which result in the GRN performing different logic gate functions. Finally, the parameter values of the GRN are set such that the GRN performs a first logic gate function.

Another embodiment of the inventive methods is a method for creating a logic gate comprising identifying a construct, which is a gene regulatory network, as bistable and nonlinear. A first well of the construct corresponds to a first set of values of an output parameter of the construct, and a second well corresponds to a second set of values of the output parameter. The method next comprises determining an optimal level of noise for the construct. The method further comprises determining a set of data inputs to the construct, with the set of data inputs being mapped onto a set of logical inputs. The method yet further comprises determining at least one tunable control parameter to the construct such that, when the construct experiences the optimal level of noise, applying the tunable control parameter causes the construct to have a logic gate functionality. The method still further comprises determining a logical output by determining an output state of the construct by measuring the output parameter of the construct as a function of the data inputs. If the measured value is of the first set of values, the logical output has a first value, and if the measured value is of the second set of values, the logical output has a second value. The logical output is predictable, given the values of the set of logical inputs, according to a truth table corresponding to the logic gate functionality.

Yet another embodiment of the inventive methods comprises determining that a bistable construct is experiencing an intensity of noise within an optimal range of noise intensity values. In this embodiment, the construct comprises three operator sites that overlap a promoter region and the cI gene sufficient for transcription, translation, and degradation of a cI gene product, with a first well corresponding to a first set of values of a repressor protein concentration, and a second well corresponding to a second set of values of the repressor protein concentration. The method also comprises applying a tunable control parameter to the construct to select logic gate functionality, with the tunable control parameter being proportional to the degradation rate of a repressor cI. The method further comprises adjusting a basal rate of production of the repressor cI as a data input to the construct such that the data input encodes values of a set of logical inputs. The method yet further comprises detecting a logical output of the construct by detecting an output state of the construct by measuring the repressor protein concentration. If a measurement is of the first well, the logical output has a first value, and if the measurement is of the second well, the logical output has a second value. The logical output is predictable, given the values of the set of logical inputs, according to a truth table corresponding to the logic gate functionality.

BRIEF DESCRIPTION OF THE DRAWINGS

Throughout the several views, like elements are referenced using like references. The elements in the figures are not drawn to scale and some dimensions are exaggerated for clarity.

FIGS. 3A-3D are truth tables.

FIGS. 6A & 6B are plots of the potential function U(x).

FIGS. 14A-14B are performance graphs showing the performance of different logic gates.

FIGS. 17A-17B are plots representing the performance of logic gates.

DETAILED DESCRIPTION OF EMBODIMENTS

Figure 1:
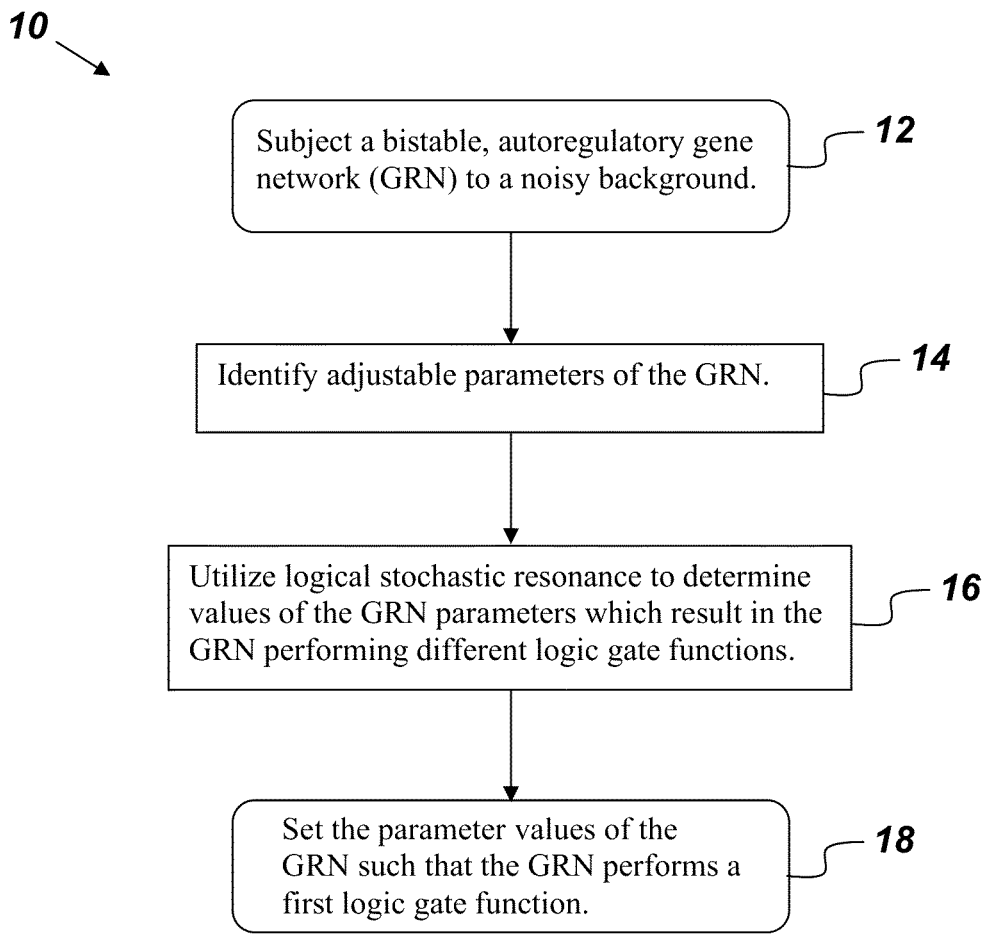
FIG. 1 is a flowchart of a method for providing a biological logic gate.

FIG. 1 is a flowchart highlighting steps of a method 10 for providing a biological logic gate. The first step 12 of the method 10 provides for subjecting a multistable construct to a noisy background. A construct is any gene regulatory network (GRN) or any subpart of a gene regulatory network. A construct is nonlinear, and in particular circumstances, it can behave as a logic gate. The construct behaves consistently and robustly as a logic gate when the construct is subjected to a non-zero level of noise intensity, though such an effect is counterintuitive. The next step 14 provides for identifying adjustable parameters of the GRN. The next step 16 provides for using logical stochastic resonance (LSR) to determine values of the GRN parameters which result in the GRN performing different logic gate functions. The next step 18 provides for setting the parameter values of the GRN such that the GRN performs a first logic gate function. The method 10 may be applied to any GRN that is at least bistable.

Provided below is a description of an embodiment of method 10 wherein the GRN is a synthetic gene network derived from the bacteriophage λ. Method 10's application of the LSR paradigm exploits existing noise and the nonlinearity of the GRN to create a reconfigurable logic gate. This biological logic gate can emulate or "morph" the logical gate functions such as AND and OR operations through varying internal system parameters, in a noisy background. In other words, method 10 provides a way to create a logic gate in an engineered genetic network in which the actual function of the gate can be changed after the network has been built, via an external control parameter.

In synthetic biology, the goal is to study the cell dynamics at the genetic level, using the electrical engineering approach. Genetic engineering with recombinant DNA is a powerful and widespread technology that enables biologists to redesign life forms by modifying or extending DNA. Advances in this field allow scientists to gain insight into the operating principles that govern living organisms. In the field of electrical engineering, with the present tendency to scale down each element in the circuit toward the nanometer region, noise has become an element that cannot be eliminated or neglected. Noise is relevant to both circuit characterization and functionality. For instance, the noise immunity in an electrical circuit has become the recurring objective of significant research efforts in this field. Similarly, in biology, when working in nano-scale dimensions and with a small number of elements, small fluctuation may largely affect the system behavior. In traditional circuits, noise can cause logic gates to fail and not behave according to truth tables. The common approach is to find a solution that reduces the noise intensity in order to obtain as stable and predictable a performance as possible.

Consequently, it is counterintuitive that noise would enhance the stability and predictability of a circuit. Instead of conceiving noise as a disturbance, method 10 exploits the noise. In order to experience this effect, a nonlinearity—such as a bistable potential function—and a noisy signal have to be present. In our particular case, the input signal is not added to the nonlinear function that characterizes the system, but rather it is encoded by adjusting a parameter of the nonlinear function. The noise enhancement effect occurs in a range of optimal noise. For illustration, let us consider a nonlinear function, in particular a bistable potential energy function.

Figure 2:
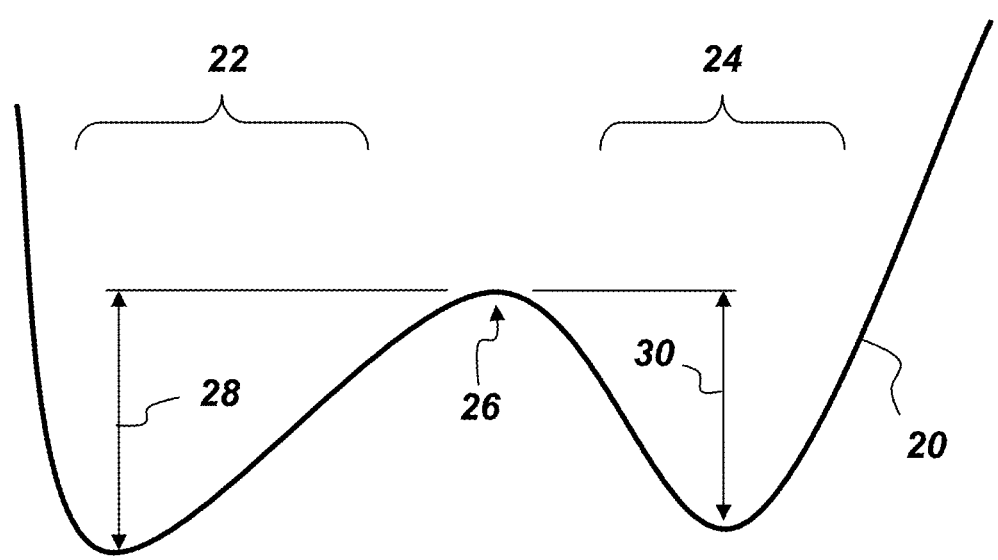
FIG. 2 is a depiction of a bistable function.

FIG. 2 is an illustration of a bistable potential energy function 20. Because it is bistable, the shape of the potential function 20 will have two steady states, (we can define them as the left potential well 22 and the right potential well 24) and an unstable state 26, which lies between the two steady states. The difference between the unstable state 26 and the bottom of the left well 22 is referred to as the first barrier 28. The difference between the unstable state 26 and the bottom of the right well 24 is referred to as the second barrier 30.

If the potential energy function 20 is symmetric, the calculated first barrier 28 is equal to the calculated second barrier 30. On the contrary, if the potential function 20 is asymmetric, the two barriers will have different values. Moreover, if the noise intensity is comparable to a given barrier value, the system will have the correct amount of energy to randomly overcome the given barrier and to change its well. For the logic gate functionality, an asymmetric configuration of the potential energy function 20 is preferable. In accordance with a truth table, the desired output state is characterized by a deeper barrier. Now consider a noise intensity that allows the system to switch from the "wrong" stable state to the "correct" stable state (the one with a deeper barrier). The same noise intensity will not be sufficient to let the system to switch back in a reasonable time (because the "correct" well will have a deeper barrier, higher than the noise intensity value). Finally, the measured output state will be the one according to the truth table. This behavior is not only restricted to a genetic regulatory network, but to all physical systems that are nonlinear (bistable), in presence of noise and with an input signal, as described in K. Murali, S. Sinha, W. L. Ditto, and A. R. Bulsara Phys. Rev. Lett. 102, 104101 (2009), which is incorporated by reference herein.

For any given GRN, there is a range of magnitudes of inherent noise that, when experienced by the GRN, creates an acceptably high probability of the GRN realizing the logic gate functionality. One example GRN is composed by three operator sites that overlap a promoter regions and the cI gene sufficient for transcription, translation, and degradation of a cI gene product. The GRN may be another autoregulatory gene network that is robust and fast. The GRN may also be a toggle switch, or two-gene network.

To function as a logic gate, a GRN must have multiple wells that can encode different logical outputs. This characteristic of a GRN is multistability, or the GRN being multistable. The most basic multistability that a GRN can possess in order to operate as a logic gate is bistability, that is, the GRN is bistable, or having two wells. The various wells of a GRN may correspond to distinct ranges of values of an output parameter of the GRN. To determine what logical state a GRN is in, the output parameter is measured and compared to the ranges of values that define particular wells. For example, the different output states may correspond to different wells of the potential energy function 20 of the GRN. For instance, the left well 22 of the GRN may correspond to a first set of values of an output parameter of the GRN and the right well 24 of the GRN may correspond to a second set of values of the output parameter.

For a bistable GRN, an output parameter having a value within the first set of values—corresponding to the left well 22—may correspond to one logical output, such as zero. Likewise, an output parameter having a value within the second set of values—corresponding to the right well 24—may correspond to another logical output, such as one. For a GRN having more than two wells, multiple wells could correspond to the same logical output, provided that there were two distinct sets of wells to correspond to the logical outputs of zero and one.

In the cI gene region example, the GRN is bistable, and the output parameter is the repressor protein concentration. A first set of values of the repressor protein concentration, values below a defined threshold value, may be understood to correspond to a logical output of zero, and a second set of values of the repressor protein concentration, values above the defines threshold value, may be understood to correspond to a logical output of one. The repressor protein concentration, x, corresponds to the potential energy function 20 of the cI gene region example, which may be expressed as function $U(x)$, which is an asymmetric potential energy function with a left well and a right well such as is depicted in FIG. 2. The defined threshold value is a value between the minima described by the left well 22 and the right well 24. Put another way, the defined threshold value is at or near the top of the unstable state 26 separating the wells. With such a potential energy function, the GRN will tend towards a steady state in one or the other well and by measuring the repressor concentration and comparing that measurement to the defined threshold value, the current well, or state, of the GRN may be determined. Examples of potential energy functions for gene regulatory networks are described in J. Hasty, J. Pradines, M. Dolnik, and J. J. Collins, Proc. Natl. Acad. Sci. U.S.A. 97, 2075 (2000); J. Hasty, F. Isaacs, M. Dolnik, D. McMillen and J. J. Collins, Chaos 11, 207 (2001); and F. J. Isaacs, J. Hasty, C. R. Cantor, J. J. Collins, Proc. Natl. Acad. Sci. U.S.A. 100, 7714 (2003), all of which are incorporated by reference herein.

FIGS. 3A-3D depict truth tables that correspond to various logic gates. Columns A and B represent logical inputs, and column X represents a logical output. A tunable control parameter, referenced herein as $\gamma$, controls the logic gate functionality of the GRN. Different values of the tunable control parameter $\gamma$ correspond to different types of logical gate functionality. For example, a GRN may have a tuning input that selects among AND, OR, NAND, and NOR gate functionality.

In the cI gene region example, $\gamma$ is a value proportional to the degradation rate of cI which takes on two distinct values, one corresponding to OR gate functionality and one corresponding to AND gate functionality. In alternate embodiments, $\gamma$ is a value proportional to the degradation rate of cI which takes on two distinct values, one corresponding to NOR gate functionality and one corresponding to NAND gate functionality.

In addition to the tunable control parameter, the GRN may also take in data inputs. Data inputs are environmental conditions or stimuli that encode sets of logical inputs, which, depending on the logic gate functionality of the GRN, are processed to create a logical output. In the cI gene region example, data inputs correspond to a basal rate of production of the repressor cI and are expressed as a. The specific environmental conditions or stimuli applied to a GRN may constitute either the data inputs to or the tunable control parameter of the GRN. For example, these inputs or parameters may be controlled by, for example, changing the temperature or exposing the GRN to UV light.

After the inputs are applied to the GRN, some time should be allowed pass before the outputs are measured to allow the biological changes underlying changes between logical states to occur. Exactly how much time is necessary may be dictated by characteristics of the dynamical evolution of the particular GRN. For example, for the autoregulatory gene network embodiments, the time between application of the input and the measurement of the output must be longer than the degradation time and the dilution time.

The implementation of biological circuits such as memory devices, switches, oscillators, amplifiers, etc. is possible through the regulation of cellular functions at the gene level. To achieve this task, a theoretical modeling of the gene expression dynamics is required. For a complete analysis, two important ingredients cannot be removed and have to be considered: nonlinearity and random fluctuations. For example, in many natural systems it is often assumed that noise has a negative influence on cellular processes and should be avoided when engineering genetic circuits that require exquisite control. In general, however, the delicate interplay between noise and nonlinearity should be well-characterized for an optimal understanding/prediction of the system performance. This is particularly true in natural systems wherein the noise is, quite often, the "signal" (rather than simply a laboratory curiosity) or the driving force that lets the system change its state.

As one might expect, depending on the goal, external noise and fluctuations at the genetic level can either be undesirable or useful. Genetic circuits (whether naturally occurring or synthesized) have to be reliable, robust and predictable; this is best achieved through exploiting the interaction between noise and nonlinearity with a view to enhancing performance. A good example of this is the scenario of Stochastic Resonance (SR) where an optimal range of noise intensity can enhance the system response to weak input signals. Noise originates from many sources and is, for simplicity divided in two classes: internal and external. Internal noise includes fluctuations in the gene expression (transcription, translation and degradation), cell cycle variations, and differences in the concentrations of metabolites. The magnitude of internal noise is related to the system size, and its origin is often thermal. External noise usually originates from extrinsic environmental variations.

The intriguing novelty of LSR in a GRN is to allow a single module to be used for many different applications via adjusting the network parameters to obtain specific functionalities. We are, thus, led to study the realization of a biological logic gate with the requirement of maximal flexibility. As explained herein, with LSR one can define a large range of values that can be adjusted to switch the gate between the AND and OR configurations, and to be robust to noise. Implementing a logic gate in a GRN through the use of LSR may be achieved by introducing the Langevin equation for the repressor protein concentration with a high logic gate performance in a noisy environment.

This section provides an outline of the main features that characterize LSR. First of all, consider the basic functioning of a logic gate. Its logic input $N_i$ (where i is the number of inputs, in this case 1 and 2) can be either 0 or 1. Accordingly, there are four distinct logic input sets $(N_1, N_2)=(0, 0), (0, 1), (1, 0)$, and $(1, 1)$. The two inputs enter in the system equation as the sum $N_1+N_2=N$, the input set reduces to three combinations, with $(0, 1)$ and $(1, 0)$ yielding the same N. The output of the logic gate is determined by its state. The output could be set as 1 if it is below a certain threshold that selects one of the stable states of the system (e.g. the left potential well 22 in a bistable system such as is depicted in FIG. 2), or it can be 0 if the output value is over the threshold (e.g. the right potential well 24 of FIG. 2). Table 1 below is a truth table of the fundamental OR, AND, NOR, and NAND logic operations. Since the inputs are encoded as $N=N_1+N_2$, the input set reduces to three terms.

TABLE I

| Input Set $(N_1, N_2)$ | OR | AND | NOR | NAND |
| --- | --- | --- | --- | --- |
| (0, 0) | 0 | 0 | 1 | 1 |
| (0, 1)/(1, 0) | 1 | 0 | 0 | 1 |
| (1, 1) | 1 | 1 | 0 | 0 |

We consider now a stochastic nonlinear system:

$$\dot{x}=F(x,a,b,\ldots)+N+D_n\xi(t) \qquad (1)$$

where a and b characterize the generic nonlinear function F given, in the deterministic system by the negative gradient of a potential function with two stable attractors (in this paper, we consider fixed point attractors corresponding to a bistable potential). The second term in Eq. (1) is the input signal that can assume the values reported in Table I. Finally, $\xi(t)$ represents additive zero mean Gaussian noise with unit variance, and intensity parameter $D_n$ (typically, $D_n$ would be the standard deviation).

Assume that random fluctuations have correlation time scale smaller than any other reaction time scale in the system, so that the noise can be taken to be delta correlated (i.e., <$\xi(t)\xi(t')$>=$\delta(t-t'))$. The case of state-dependent (or multiplicative) noise will be addressed later in this work. The LSR paradigm affords the possibility to exploit noise in order to get a desired logic gate performance with almost unit probability i.e., the operation is rendered quite reliable even in the noisy environment. Indeed, in a given range of noise intensity values, the performance of the system is optimized and its output is the logical combination of the two input signals. Thus, the LSR paradigm underpins the realization of morphable and reliable logic gates in the presence of noise: changing parameters such as a and b, or applying a controllable dc asymmetrizing system to the dynamics Eq. (1), one can switch from the AND to the OR gate. Hence, LSR is a practical and reasonable paradigm to be applied in computational devices wherein the noise-floor cannot be suppressed.

The complex functions of a living cell are carried out through the concerted activity of many genes and gene products. This activity is often coordinated by the organization of the genome into regulatory networks. The DNA in genomes does not direct protein synthesis itself, but instead uses RNA polymerase as an intermediary. In particular, the RNA polymerase will bind in a specific segment of the DNA, known as the promoter region. An mRNA is then produced when the RNA polymerase molecule initiates transcription at the promoter level, synthesizes the RNA by chain elongation, stops transcription at a terminator, and releases both the DNA template and the mRNA molecule. Therefore, one can speak of the promoter as the most important point of control of a specific gene expression. Afterwards, mRNA is decoded by the ribosome to produce a specific amino acid chain that, later, folds into an active protein. Among all proteins, gene regulatory proteins switch the transcription of individual genes on and off. They usually bind the DNA in specific regions close to the RNA polymerase start site and, depending on the nature of the regulatory protein and the location of its binding site relative to the start site, either activate or repress transcription. The time and the place that each gene is transcribed, as well as its rate of transcription under different conditions, are determined by the spectrum of gene regulatory proteins that bind the regulatory region of the gene. These reactions are controlled by feedback loops that arise when the translated protein is capable of interacting with the promoter(s) of other genes. Feedback can occur in the positive (activation) or negative (repression) sense.

Typically, one can find proteins in a homodimer or heterodimer form that is responsible for the presence of a nonlinearity in genetic networks. In this work we adopt an engineering approach in describing the design of a synthetic network present in the virus bacteriophage $\lambda$. Because of the complexity of the whole system, we have focused our study on a solitary gene network (or autoregulatory gene network). This restriction has two advantages. In principle it affords the possibility of better prediction of the system dynamics via a mathematical formulation and, thus, an understanding of the cellular behavior. Secondly, a deeper knowledge of the simple autoregulatory network taking noise into account can lead to several applications which exploit the noise, such as LSR. Bacteria and their temperate phages, e.g. *Escherichia coli* (*E. coli*) and $\lambda$, exist in symbiotic relationships. After the $\lambda$ phage infects the bacteria, the evolution of the $\lambda$ phage proceeds down one of the two pathways: lytic and lysogenic. Each pathway depends on the controlled sequential synthesis and subsequent activity of $\lambda$-encoded proteins. Lytic infection by the phage $\lambda$ results in the release of hundreds of new phages per infected cell. The minimum set of events in the growth cycle is, therefore, DNA replication, phage particle synthesis, and cell lysis. The creation of new phage progeny can, then, infect other bacteria. In the lysogenous pathway, the temperate phage induces a change in the phenotype of the infected bacteria through the incorporation of the phage DNA into the host genome. The newly integrated genetic material, called a prophage, can be transmitted to daughter cells at each subsequent cell division, and a later event (such as UV radiation) can release it, causing proliferation of new phages via the lytic cycle.

The key section of the decision between one of the two pathways lies in the right operator region ($O_R$), in which three DNA-binding sites are recognized by two phage encoded regulatory proteins: the lambda-repressor protein (also called CI) and Cro. $O_{R1}$, $O_{R2}$ and $O_{R3}$, the three operator sites, overlap the promoter regions of the genes that encode these same proteins: the $P_{RM}$ (where RM is repressor maintenance) promoter controls the expression of cI and the $P_R$ (where R is repressor) promoter controls the expression of Cro. The pattern of CI/Cro binding to the three operator sites determines whether the lysogenic or lytic pathway will be followed. Hence, the bacteriophage $\lambda$ displays bistability in the choice of one of two pathways, with the characteristics of its stable attractors adjustable by externally changing the system parameters.

In this example embodiment of method 10, we focus only on the regulation of the $P_{RM}$ operator region in a DNA plasmid: an autoregulatory network that shows a binary decision-making through a positive feedback loop. In this feedback loop, $O_{R1}$, $O_{R2}$ activate transcription, while $O_{R3}$ represses transcription. The repressor protein a binds to the DNA in one of the three $O_{Ri}$ sites. CI is expressed by the gene a and subsequently dimerizes. Depending on the binding affinities, binding happens as follows: the dimer first binds to the $O_{R1}$ site, then to $O_{R2}$ (where a downstream transcription is enhanced) and, finally, to $O_{R3}$ (that effectively turns off the protein production).

Figure 4:
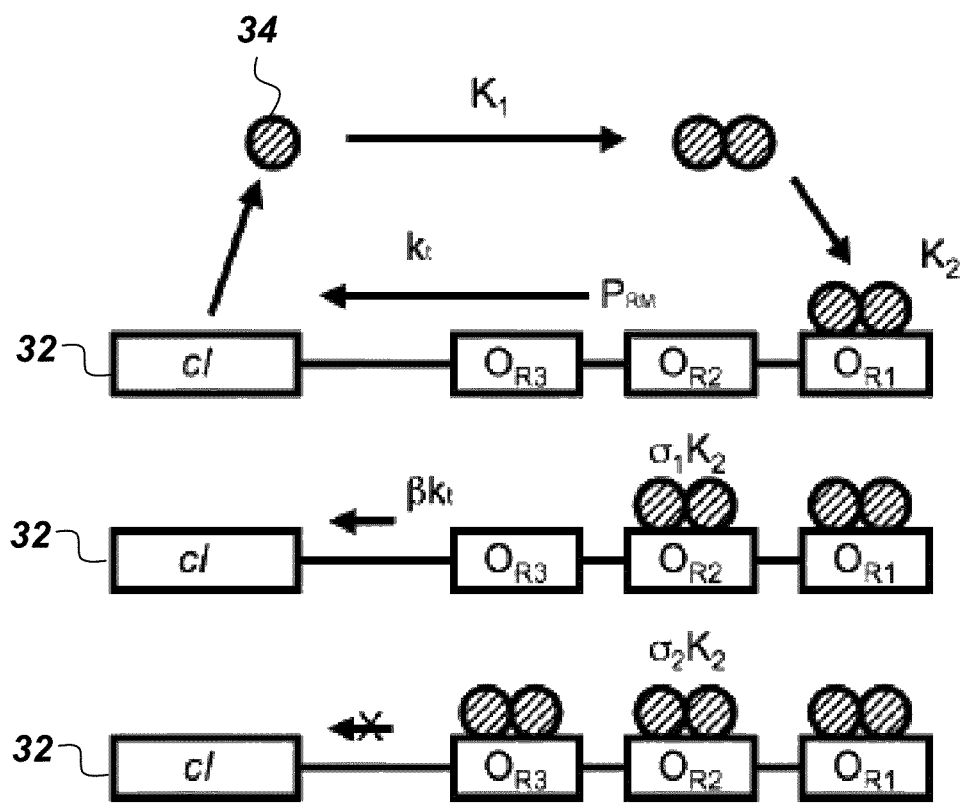
FIG. 4 is an illustration of a gene autoregulatory network.

FIG. 4 is an illustration of a GRN 32, where the promoter region contains three operator sites ($O_{R1}$, $O_{R2}$, and $O_{R3}$). The cI gene expresses the $\lambda$ repressor protein 34, which in turn dimerizes and then binds to the operator sites. For a complete comprehension of the autoregulatory gene network described above, we have developed a quantitative model. Consider, firstly, the biochemical reactions that characterize our network. These reactions are categorized depending on the order of the rate at which they occur. The ones that have a rate constant of the order of seconds (fast reactions) are considered to be at equilibrium; such reactions are referred to as multimerization, or, as the binding between the dimer and the operator site. The other reactions with rates of the order of minutes are considered slow reactions. Here we list the fast reactions used to describe our model:

where X, $X_2$, D, and $D_i$ are the repressor monomer, the repressor dimer, the DNA promoter region, and the dimer binding to the $O_{Ri}$ operator site, respectively. Moreover, each fast reaction is characterized by an equilibrium constant ($K_i=k_i/k_{-i}$, where $k_i$ and $k_{-i}$ are the rate constant): $K_1$, $K_2$, $K_3=\sigma_1 K_2$, and $K_4=\sigma_2 K_2$, in order from the first to the fourth equation in (2). The variables $\sigma_1$ and $\sigma_2$ represent the binding strengths relative to the dimer-$O_{R1}$ strength. In addition to (2), we have to consider the slow reactions: transcription, degradation and dilution.

We assume that dilution due to cell growth is, likely, slower than monomer degradation, but comparable (in timescale) to transcription. These reactions are irreversible. In particular, if one repressor dimer binds to the first right operator site ($O_{R1}$), transcription proceeds at the basal rate. Moreover, an amplification of transcription occurs when a subsequent repressor dimer binds to $O_{R2}$: the binding affinity to the RNA polymerase is increased by a factor $\beta$. We write the reactions governing these processes as $$D_1 + P \to D_1 + P + nX$$

$$D_2 D_1 + P \to D_2 D_1 + P + nX$$

$$X \to \phi$$

$$X_2 \to \phi \quad (3)$$

where each of the listed reactions in (3) are characterized by a rate constant: $k_t$ (for transcription rate while one dimer is bound to the $O_{R1}$ operator site), $\beta k_t$ (for transcription enhanced by a factor $\beta$), $k_x$ (for degradation) and $k_y$ (for dilution). The variable P denotes the concentration of RNA polymerase, and n is the number of repressor proteins per mRNA transcript. While the reaction rates are embodied by rate laws (as equations (2) and (3)), the biochemical dynamics can be described with differential equations. If we consider high copy-number plasmids, the dynamics in this gene network can be described by the evolution of the $\lambda$ repressor concentration in the monomer and dimer form as follows:

$$\dot{x} = -2k_1 x^2 + 2k_{-1} x_2 + nk_t p_0 (d_1 + \beta d_2) - k_x x + \epsilon d_0$$

$$\dot{x}_2 = k_1 x^2 - k_{-1} x_2 - k_y x_2 \quad (4)$$

where we assume that the concentration of the RNA polymerase $p_0$ to be constant and $\epsilon$ is the basal expression rate. In particular, the concentrations in our system have been defined as $x = [X]$, $x_2 = [X_2]$, $d_0 = [D]$, $d_1 = [D_1]$, $d_2 = [D_2 D_1]$, and $d_3 = [D_3 D_2 D_1]$. The first equation in (4) may be simplified as follows:

$$\dot{x} = -2k_1 x^2 + 2k_{-1} x_2 + nk_t p_0 d_1 + nk_t p_0 \beta d_2 - k_x x + \epsilon d_0 =$$

$$= -2k_1 x^2 + 2k_{-1} x_2 + (nk_t p_0 - \epsilon + \epsilon) d_1 + (nk_t p_0 \beta - \epsilon + \epsilon) d_2 - k_x x + \epsilon d_0 =$$

$$= -2k_1 x^2 + 2k_{-1} x_2 + (nk_t p_0 - \epsilon) d_1 + (nk_t p_0 \beta - \epsilon) d_2 - k_x x + \epsilon (d_0 + d_1 + d_2 + d_3) - \epsilon d_3 \quad (5)$$

Moreover, for the fast reactions in Eq. (2), that are considered at equilibrium, the mathematical formulation is:

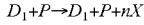
$x_2 = K_1 x^2$,

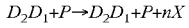
$d_1 = K_1 K_2 d_0 x^2$,

$d_2 = \sigma_1 (K_1 K_2)^2 d_0 x^4$,

$d_3 = \sigma_1 \sigma_2 (K_1 K_2)^3 d_0 x^6 \quad (6)$

In addition, we also consider the total concentration of DNA promoter sites $d_T$ to be constant (where the subscript T refers to total). This can be written as:

$$d_T = d_0 + d_1 + d_2 + d_3 \quad (7)$$

and at the same time $\epsilon d_T = r$ is constant. We can now explicitly calculate $d_0$ from (6) and (7):

$$d_0 = \frac{d_T}{1 + K_1 K_2 x^2 + \sigma_1 (K_1 K_2)^2 x^4 + \sigma_1 \sigma_2 (K_1 K_2)^3 x^6} \quad (8)$$

The dimerization reactions are the faster reactions; this has allowed us to simplify the system. Under these assumptions, the first two terms of both equations in (4) will cancel. However, this will leave only one negative term on the right hand side of the second equation. To accurately model the evolution of the chemical species x, we define the variable $x_{tot} = x + 2x_2$; this represents the total number of biomolecules in the system, either dimer (where two molecules are consumed) or monomer (where one molecule is consumed). Then, equations (5)-(8) can be reorganized as:

$$\dot{x}_{tot} = \dot{x} + 2\dot{x}_2 = \frac{d_T (K_1 K_2 (nk_t p_0 - \epsilon) x^2 + (nk_t p_0 \beta - \epsilon)(K_1 K_2)^2 \sigma_1 x^4 - \epsilon \sigma_1 \sigma_2 (K_1 K_2)^3 x^6}{1 + K_1 K_2 x^2 + \sigma_1 (K_1 K_2)^2 x^4 + \sigma_1 \sigma_2 (K_1 K_2)^3 x^6} + r - k_x x - 2K_1 k_y x^2 \quad (9)$$

To work in terms of the repressor concentration in the monomer form, we can, explicitly, write the left hand side of Eq. (9):

$$\dot{x}_{tot} = \dot{x} + 2\dot{x}_2 = \dot{x} + 4K_1 x \dot{x} = (1 + 4K_1 x) \dot{x} \quad (10)$$

where the relation between x and $x_2$ has been shown in Eq. (6). We can now divide by $(1 + 4K_1 x)$ on the left and right hand sides of Eq. (9). Further, without loss of generality, we can define the dimensionless variables $$\bar{x} = x \sqrt{K_1 K_2} \text{ and } \bar{t} = t r K_2 / 4.$$

Under these assumptions, and after some calculations, we obtain the dimensionless equation (we have suppressed the overbar on x and t):

$$\dot{x} = \frac{(\alpha - 1) x^2 + \sigma_1 (\alpha \beta - 1) x^4 - \sigma_1 \sigma_2 x^6}{(\tau + x)(1 + x^2 + \sigma_1 x^4 + \sigma_1 \sigma_2 x^6)} + \frac{1 - \gamma x - \gamma_y x^2}{\tau + x} \quad (11)$$

where we introduce the dimensionless parameters $$\tau = \sqrt{K_1 K_2} / 4 K_1.$$

$$\alpha = nk_t p_0 d_T / r, \; \gamma = k_x / (\sqrt{K_1 K_2} \, r), \; \gamma_y = 2k_y / (r K_2),$$

In Eq. (11) the first term on the right-hand-side is related to the expression of the repressor protein because of transcription. The $x^2$, $x^4$, and $x^6$ terms are due to the dimerization of the $\lambda$ repressor and the subsequent binding to the operator sites. The $x^6$ term represents, for example, the occupation of all three operator sites. The second term includes the basal expression rate (while there is no binding to the DNA), the degradation and the dilution that have the role of reducing the protein concentration in the cell. Moreover, in this example embodiment of method 10, we set values for the constants that are relevant to this autoregulatory network as detailed in Table II. Constants may be selected from Table II such that calculations are within the space of biologically accessible parameter ranges.

Eq. (11) is a deterministic dynamical model, the right-hand-side of which is the function F in Eq. (1), and α and γ are particular examples of the listed parameters (a and b, . . . ) in Eq. (1). Although it seems complex and contains several nonlinear terms, the potential function characterizing the system is bistable in a particular range of parameters, as will be shown below. In other words, the repressor concentration can assume (with a high probability) two favorable values (the minima in the potential function) that correspond to lytic or lysogenic pathways.

TABLE II

| Parameter Value | Meaning |
|---|---|
| β = 11 | Degree of transcriptional activation |
| K1 = 5.0 × 107M−1 | Equilibrium constant for dimerization |
| K2 = 0.33 × 107M−1 | Equilibrium constant for dimer-OR reaction |
| σ1 = 2 | Binding affinity for the dimer to OR2 relative to OR1 |
| σ2 = 0.08 | Binding affinity for the dimer to OR3 relative to OR1 |

A modified version of the LSR paradigm may be used with method 10. The modification is desirable because of the unique (highly asymmetric) structure of the potential energy function that characterizes this system; the conventional LSR paradigm yields somewhat sub-optimal performance in this case. These calculations relate to the space of biologically relevant parameters; these parameters include the system (additive or multiplicative) noise parameters. The modified version of the LSR paradigm introduces two significant changes. Firstly, we have characterized LSR in an autoregulatory network not only in the additive noise regime (as in Eq. (1)), but also in the multiplicative noise case. Therefore the dynamical equation takes the more general form:

$$\dot{x} = F(x, a, b \ldots, D_m \eta(t)) + D_n \xi(t) \quad (12)$$

where η(t) is a multiplicative zero-mean Gaussian noise with unit variance and intensity parameter $D_m$. In general, this noise can affect one or more parameters (listed with symbols a and b above) and, consequently, the system "energy landscape." While the multiplicative noise intensity $D_m$ is different from zero, the term F will be a stochastic nonlinear function. In addition, we have to make clear that, for a concrete application of LSR to a biological model, the set of logic gate inputs are not added as in Eq. (1) but are, instead, implemented through the parameter values such as a, b, etc. (in the specific biological system of this work, the parameters are α and γ, see Eq. (11)).

In the embodiment described above, we tried to enhance the logic gate performance and to enlarge the noise intensity range where it is possible to implement LSR in this particular gene network since the biological model we are using does not yield enough dynamical range to successfully implement the (conventional) LSR paradigm. The conventional LSR paradigm deals with abstract mathematical models with full control over the system dynamics, in particular the depth and width of the potential wells; hence, the dynamical system may be adjusted so as to neatly fit the requirements of (conventional) LSR. For example, in conventional LSR, the system parameters (a, b, . . . ) may be chosen to provide well-defined bistability for all the distinct logic input sets given in the truth Table I.

Figure 5:
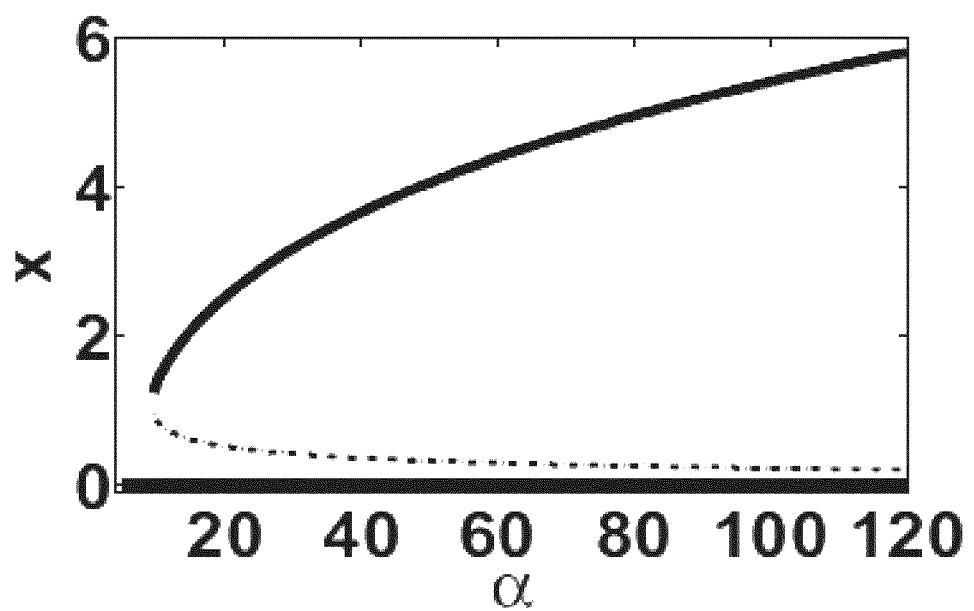
FIG. 5 is a plot of a bifurcation diagram for a general function F.

FIG. 5 is a plot of a bifurcation diagram for the general function F in Eq. (11) vs. α (that is one of the two parameters we will use to implement the logic gates); in this case, the α range for reliable implementation of the conventional LSR paradigm is over ten, to insure the bistability. In FIG. 5, the bistable behavior is visible for a fixed value of γ=50. The modified version of LSR is to choose the parameters of the model so that the undesired well (almost) disappears, and to take advantage of stochastic resonance for the cases where one cannot, simply, remove the unwanted well from the system potential function, U(x). This second case usually happens when the inputs are (0,1)/(1,0). With this proposed model we simply want to take into account all the range of the parameter values that represents all the possible biological configurations. Put differently, there is the possibility that the (0,0) or (1,1) cases can be realized when U(x) is monostable.

FIGS. 6A-6B are plots of the potential function U(x) for the three input sets and for the AND gate (FIG. 6A) and OR (FIG. 6B) gate using the modified version of the LSR paradigm. The solid-line curve in both plots shows the (0,0) case and corresponds to the monostable configuration. The long-dashed curve represents the (0,1)/(1,0) cases. The dotted curve is for the (1,1) case. Through the parameter γ, then, we can deepen either well in U(x), selectively, to switch from one logic gate to the other; hence when the noise intensity is within an acceptable range of noise intensity values, trajectories will switch to the deeper well and remain there, giving rise to better performance. The modified LSR paradigm will work in a broader range of parameters than conventional LSR. Considering FIG. 5, the possible working range can now be extended to a higher than five.

The study of cells and their inner dynamics has revealed the presence of noise as a relevant element for the complete characterization and knowledge of the system itself. In this section we will focus only on the external noise source. If we consider our variable x to be the repressor protein concentration as described above, we can characterize the noise as random alterations (i.e. fluctuations) of the "background" repressor production. For the construction of our stochastic model, we suppose that these random fluctuations will affect the basal production term r. Moreover, we consider that such external effects will be small and, therefore, can be treated as a random additive perturbation to the deterministic dynamics (see Eq. (11)):

$$\dot{x} = \frac{(\alpha-1)x^2 + \sigma_1(\alpha\beta-1)x^4 - \sigma_1\sigma_2 x^6}{(\tau+x)(1+x^2+\sigma_1 x^4 + \sigma_1\sigma_2 x^6)} + \frac{1-\gamma x - \gamma_y x^2}{\tau+x} + D_n \xi(t) \quad (13)$$

where ξ(t) is the additive (external) zero-mean Gaussian noise (<ξ(t)>=0), and <ξ(t)ξ(t')>=δ(t−t'), with $D_n$ being the noise standard deviation parameter (as already introduced above).

From Eq. (13) we can get the corresponding Fokker-Planck Equation for P(x, t), the probability of finding the system in a state with concentration x at the time t:

$$\frac{\partial P(x,t)}{\partial t} = -\frac{\partial}{\partial x}[F(x)P(x,t)] + D_n \frac{\partial^2}{\partial x^2} P(x,t) \quad (14)$$

where F is the nonlinear function in the right-hand-side of Eq. (11). Then the steady-state probability density function is given as:

$$P_S(x) = N_{add} \exp\left[-\frac{U(x)}{D_n}\right] \quad (15)$$

where we obtain the potential shape U(x) from the definition of F(x)=−∂U(x)/∂x; the "particle-in-potential" analogy leads us to view U(x) as an "energy landscape" wherein x(t) is the position of a hypothetical "particle" following the stochastic dynamics (13). U(x) is bistable in a parameter range and the concentration x has fixed values at the minima of U(x). $N_{add}$ is the normalization constant resulting from making the integral of $P_S(x)$ over all x equal to unity. In FIGS. 6A-6B, we have plotted the potential U(x) for a particular combination of parameter values. We can notice the (somewhat dramatic) asymmetry of the potential function: the left and right energy barrier heights are different, together with the curvatures in the bottom of the potential wells. In the presence of noise the system can, with different probabilities, span all the allowed x values that are biologically meaningful. If the noise intensity is very small compared to the two energy barriers, the system mainly remains confined in one of the two potential wells and randomly moves around in the minimum (i.e. intrawell motion). A larger noise intensity leads to a spreading of the distribution of the protein concentration values that x can assume. It is only in an optimal range of noise values, approximately when the noise intensity is comparable to the potential energy barrier, that the system switches to the other state, and, remains in the new state: from a biological point of view, the system has chosen the other possible pathway with respect to the one where it was prior to the switch.

To apply this model to the modified version of the LSR paradigm, we have chosen two parameters: one for encoding the logic gate inputs, α, and the other as a control variable to implement a morphable logic gate (in particular in this work, to switch from the AND to the OR gate and vice versa), γ. The plotted U(x) curves represent the most robust configuration in the limited range of parameters, α and γ, germane to the biological system. Several simulations have been made to exhaustively search (in the parameter space) those parameters that yield the best logic gate performances. For the new version of the LSR paradigm, we obtained (numerically) α=6.3, 9.8, and 13.3 (respectively for (0, 0), (0, 1)/(1, 0), and (1,1)), and γ=50, 36 to implement the AND and OR gate (respectively). After applying these α and γ values to Eq. (13), the stochastic differential equation, on the dimensionless interval [0, 7000], is integrated by the Euler-Maruyama method. In simulations, it is observed that 7000 is longer than the mean escape time required to switch from the "wrong" to the "correct" (depending on the desired logic outcome) well; this time length also ensures the expected logical output for a large number of trials. To quantify this behavior with respect to noise in this (designed) logic gate we measured its performance as defined as the ratio of success in realizing the desired gate over the total number of attempts; this ratio is the probability P(logic) of realizing the desired gate.

Figure 7:
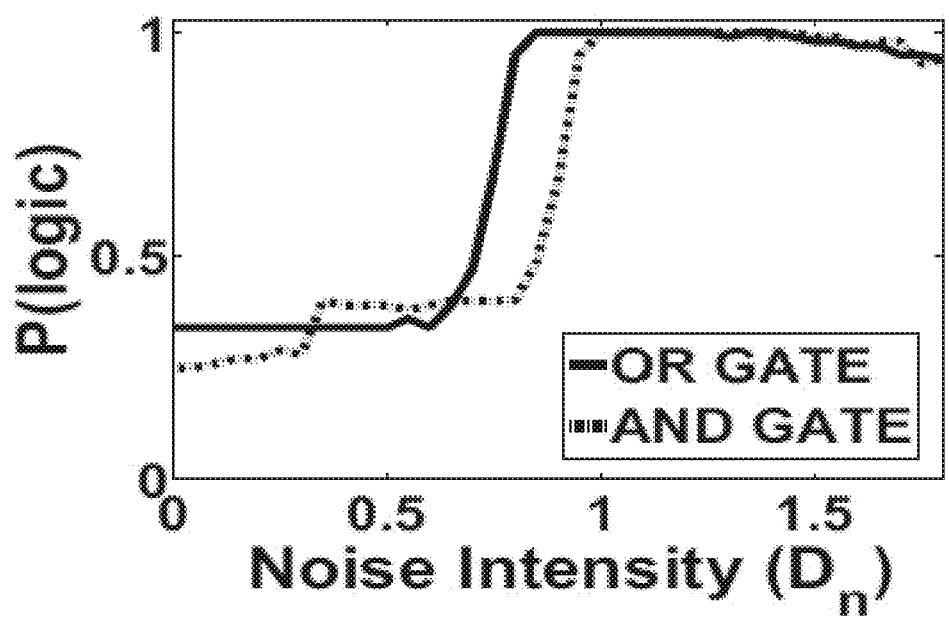
FIG. 7 is a plot of the performance of OR and AND logic gates.

FIG. 7 is a plot of the performance of OR and AND logic gates using the modified LSR paradigm, verses the additive noise intensity $D_n$. Note that for each noise value, we have checked the agreement between the simulated logical outputs for all the three data inputs ((0, 0), (0, 1)/(1, 0), (1, 1)) and the respective truth table values of the gate under study. If one of the outputs does not realize the desired gate, we mark that as a failure. If, for example, we consider one of the plots in FIGS. 6A-6B for each noise value the least robust potential configuration (among the three plotted) will have the highest influence on the performance quality of this considered gate. This procedure is repeated 500 times. The remarkable thing here, then, is that the output conforms to the truth tables in the presence of noise. More explicitly, in a relatively wide window of noise intensity, the system yields logic operations with near certainty, i.e., P(logic)~1. We can conclude that the two gates are robust to noise in the same range of noise and amenable to the design of a morphable logic gate.

Next, we note that the best performance in the logic gates can be achieved via two possible routes: changing the noise intensity or the variation of the parameter values, thereby adjusting the system dynamics to an optimal configuration, so that P(logic)~1 as desired; for a nonlinear system this is tantamount (as already noted earlier) to changing the transfer characteristic thereby "tuning" the noise.

Figure 8A:
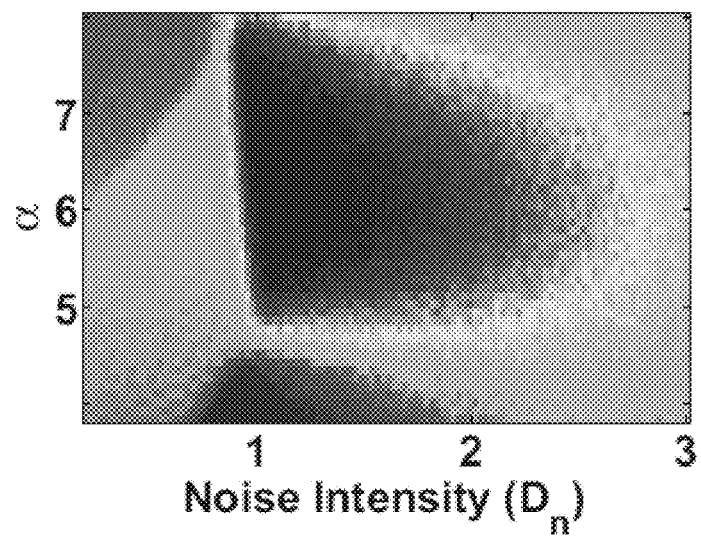
FIGS. 8A-8B are plots of noise intensities.
Figure 8B:
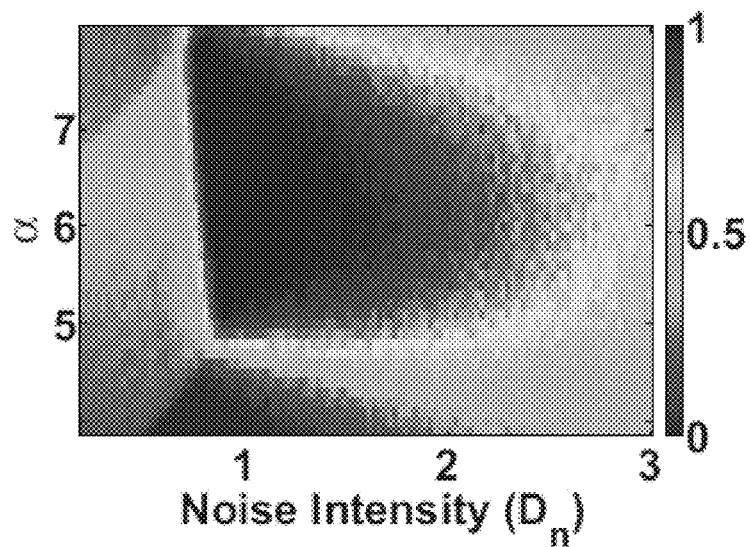

FIGS. 8A-8B are plots of noise intensities versus a values (setting γ=50 for the AND gate and γ=36 for the OR gate). FIG. 8A represents the performance of an AND gate. FIG. 8B represents the performance of an OR gate. For a fixed value of noise (for example the one mandated by nature) it is possible to select the "best" a value. It is interesting to note that (for our particular choice of model parameters) if the noise parameter $D_n$ values are in the [0.95, 1.35] regime, there is a reasonably large range of a values for which P(logic)~1, as desired. In a completely analogous way, by setting the output values in the reverse configuration, we can realize NAND and NOR gates in almost the same optimal noise intensity regime as the previous case (e.g. the left well can represent the value 1 for output of the NAND/NOR reconfigurable gate, instead of 0 as set previously for the AND/OR gate).

A complete GRN characterization necessitates extending our model to the case when the system is in presence of an internal noise source. With internal noise, we want to define all the random fluctuations that are related to the reactions inside the cell at the gene level; in other words the noise originates, in this case, from the underlying biochemical reactions rather than from external perturbations. In biochemistry, slow reactions such as translation and transcription lead naturally to large noise intensity; their rates are typically small and random fluctuations are consequently more evident. In the present section, we will consider the Langevin equation corresponding to Eq. (11), where we allow the degradation term, γ, or the transcription term, α, to fluctuate. These two cases will be discussed separately but always in presence of an (external) noisy background. In other words, method 10 deals with both the multiplicative and additive noise.

Now consider the effect of a noise source that alters the degradation rate. We vary this term, allowing the parameter γ in Eq. (11) to fluctuate, i.e., we set γ→γ–$D_m$η(t), in presence of a noisy background $D_n$ξ(t). In this way, we obtain the Langevin equation describing the evolution of the repressor protein concentration, x, $$\dot{x} = f(x,\alpha,\gamma) + h(x)D_m\eta(t) + D_n\xi(t) \tag{16}$$

where the term $D_n$ξ(t) has been detailed in Section II. The noise term η is a white Gaussian noise with a zeromean and <η(t)η(t')>=δ(t–t') and intensity $D_m$. The functions $f(x)$ and $h(x)$ represent two nonlinear functions. To investigate the effects of these noises on the genetic regulatory system, we will consider, for simplicity, that ξ(t) and η(t) in Eq. (16) are independent of each other, i.e., $$<\xi(t)\eta(t')> = <\eta(t)\xi(t')> = 0 \tag{17}$$

We now apply Eq. (16) to the autoregulatory gene network under study (see Eq. (11)). We obtain:

$$\dot{x} = \frac{(\alpha-1)x^2 + \sigma_1(\alpha\beta-1)x^4 - \sigma_1\sigma_2 x^6}{(\tau+x)(1+x^2+\sigma_1 x^4 + \sigma_1\sigma_2 x^6)} - \frac{(\gamma - D_m\eta(t))x}{\tau+x} + \tag{18}$$

$$\frac{1-\gamma_y x^2}{\tau+x} + D_n\xi(t)$$

$$= \frac{(\alpha-1)x^2 + \sigma_1(\alpha\beta-1)x^4 - \sigma_1\sigma_2 x^6}{(\tau+x)(1+x^2+\sigma_1 x^4 + \sigma_1\sigma_2 x^6)} - \frac{1-\gamma x - \gamma_y x^2}{\tau+x} +$$

$$\frac{D_m \eta(t) x}{\tau + x} + D_n \xi(t)$$

where $$f(x) = \frac{(\alpha - 1)x^2 + \sigma_1(\alpha\beta - 1)x^4 - \sigma_1\sigma_2 x^6}{(\tau + x)(1 + x^2 + \sigma_1 x^4 + \sigma_1\sigma_2 x^6)} + \frac{1 - \gamma x - \gamma_y x^2}{\tau + x} \quad (19)$$

and $$h(x) = \frac{x}{\tau + x}. \quad (20)$$

The Fokker-Planck Equation for the probability density function P(x, t) of being in the state x at time t, using the Stratonovich prescription, takes the form of:

$$\frac{\partial P(x, t)}{\partial t} = -\frac{\partial}{\partial x}[a(x)P(x, t)] + \frac{1}{2}\frac{\partial^2}{\partial x^2}[b(x)P(x, t)] \quad (21)$$

with the drift and diffusion terms given by, $$a(x) = f(x) + \frac{1}{4}\frac{\partial}{\partial x}b(x) = f(x) + \frac{1}{4}\frac{\partial}{\partial x}(D_m h(x)^2 + D_n) \quad (22)$$

$$= \frac{(\alpha - 1)x^2 + \sigma_1(\alpha\beta - 1)x^4 - \sigma_1\sigma_2 x^6}{(\tau + x)(1 + x^2 + \sigma_1 x^4 + \sigma_1\sigma_2 x^6)} +$$

$$\frac{1 - \gamma x - \gamma_y x^2}{\tau + x} + \frac{1}{4}\frac{\partial}{\partial x}\left(D_m\left(\frac{x}{\tau + x}\right)^2 + D_n\right)$$

and $$b(x) = D_m h(x)^2 + D_n = D_m\left(\frac{x}{\tau + x}\right)^2 + D_n \quad (23)$$

Equation (21) may be solved in the steady state to obtain the long-time probability density function:

$$P_S(x) = N_{mul\_\gamma}\exp(-U_g(x)) \quad (24)$$

where $N_{mul\_\gamma}$ is a normalization term, while the potential $U_g(x)$ takes the form:

$$U_g(x) = -2\int^x \frac{a(y)}{b(y)} + \ln b(x) \quad (25)$$

We have checked that, in absence of fluctuations in η (i.e. $D_m$=0), the results related to additive noise are recovered. The multiplicative noise modifies the drift term a(x) through the presence of the third term in Eq. (22). This means that noise not only influences the dynamics of our biological model, but also changes the potential shape configuration: increasing or decreasing the depth of the wells, as well as altering the locations of the fixed points. Moreover, multiplicative noise can yield noise-induced critical behavior that occurs in addition to the nonlinearity-induced bistability that just exists in the potential shape. All these rich effects, of course, are related to particular parameter values.

Figure 9A:
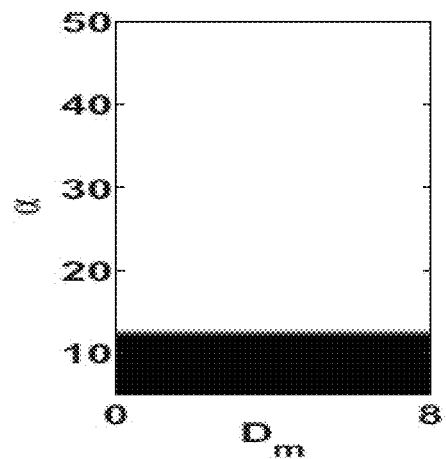
FIGS. 9A-9C are bifurcation diagrams.
Figure 9B:
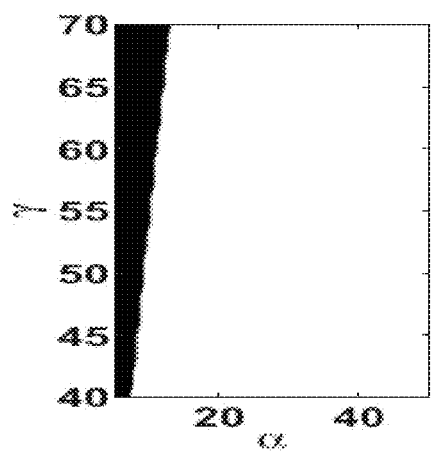
Figure 9C:
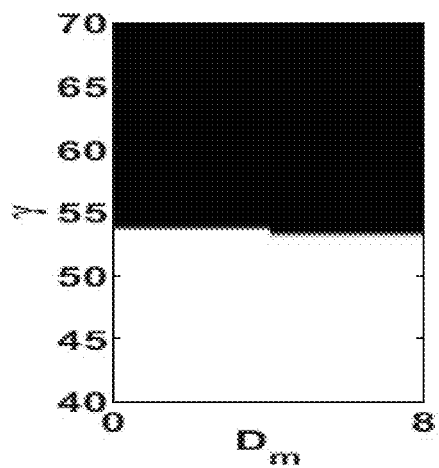

FIGS. 9A-9C are bifurcation diagrams for γ→γ−$D_m$η(t). In FIG. 9A, we varied $D_m$, and a, fixing γ=65. In FIG. 9B, we varied α and γ, fixing $D_m$=1.5. In FIG. 9C, we varied $D_m$ and γ, fixing α=10. The black area represents the bistable region, while the white area represents the monostable region. We have tested if the biological system is still robust to the presence of a multiplicative noise source while α=6.3, 9.8, and 13.3 (respectively for (0, 0), (0, 1)/(1, 0), (1, 1)), and γ=50, 36 (see previous section). We checked the P(logic) versus the additive noise intensity (as in FIG. 7), for different fixed multiplicative noise intensities. The result (not shown) is that the best α and γ values, for the additive noise case, are not anymore the best ones in this new condition (i.e. with the inclusion of multiplicative noise) for the implementation of the LSR paradigm. Thus, we are lead to study the logic gate performance versus the multiplicative noise intensity. In the presence of a random degradation rate, the system shows regions of monostability and bistability as visible in FIGS. 9A-9C. FIG. 9A represents the bifurcation diagram varying the multiplicative noise intensity $D_m$, and α, while γ and $D_n$ are fixed. In FIG. 9B, we vary γ and α, fixing the other two parameters. In FIG. 9C we plot the bifurcation diagram versus $D_m$ and γ. FIGS. 9A-9C give the range where one should, exhaustively, search for the best biological system parameters. In this case, α is the parameter used to encode the logic gate inputs, and γ the parameter for switching from the AND to the OR gate. For the new version of the LSR paradigm, we obtained (numerically) α=5, 14.5, and 24 (respectively, for (0, 0), (0, 1)/(1, 0), (1, 1)), and γ=60, 40 to implement the AND and OR gate (respectively).

Figure 10A:
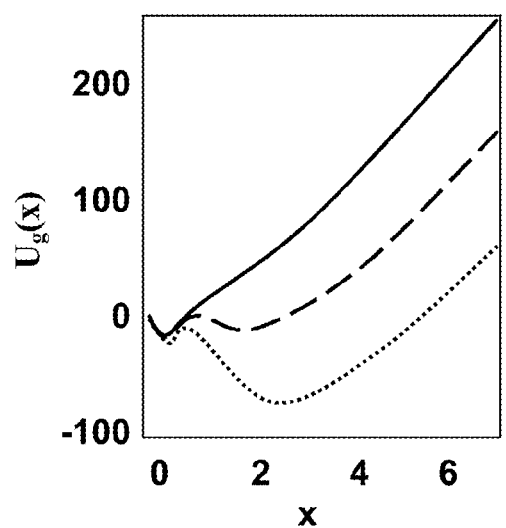
FIGS. 10A & 10B are plots of potential functions.
Figure 10B:
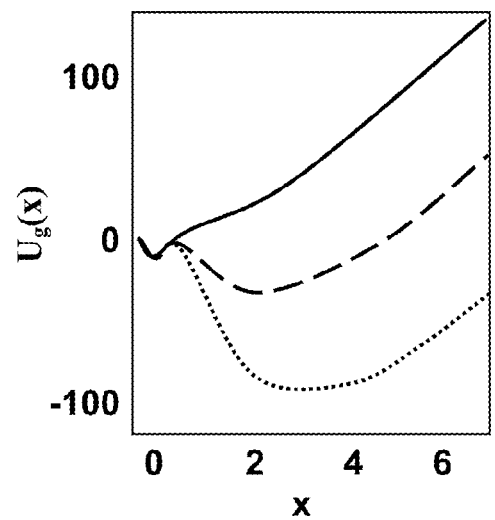
Figure 11A:
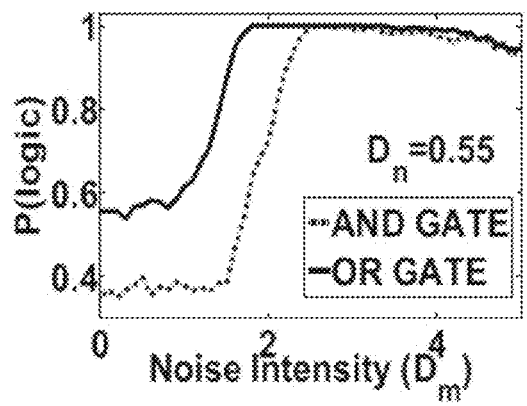
FIGS. 11A-11D are plots of noise intensities.
Figure 11B:
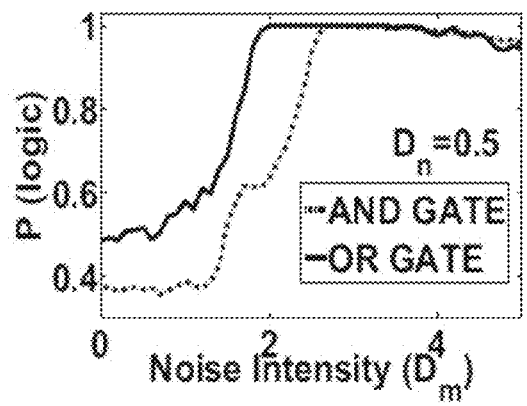
Figure 11C:
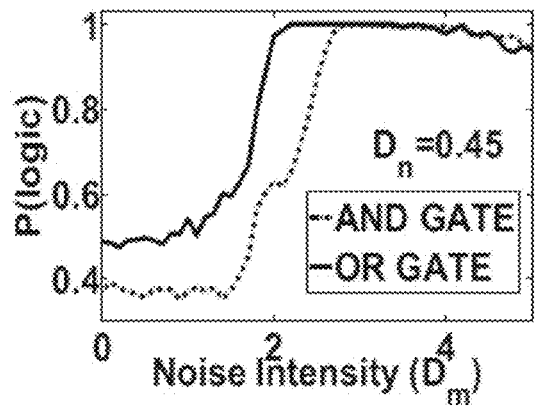
Figure 11D:
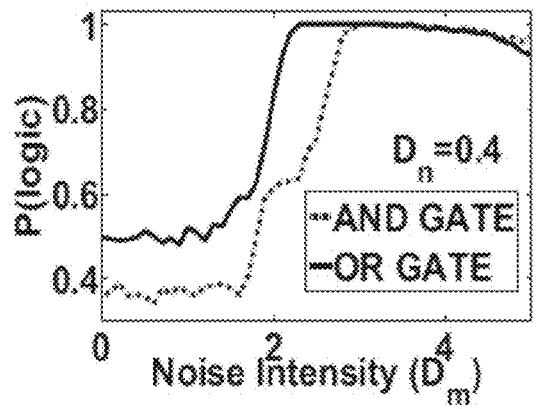

FIGS. 10A and 10B are plots of the potential functions for AND and OR gates for different data inputs. FIG. 10A is a plot of the potential function for different data inputs for an AND gate using the modified version of LSR paradigm. FIG. 10B is a plot of the potential function for different data inputs for an OR gate using the modified version of LSR paradigm. The solid curve represents the (0,0) case, the long-dashed curve represents the (0,1)/(1,0) cases, and the dotted curve is for (1,1) case. For FIGS. 10A-10B, the fixed multiplicative noise intensity is $D_m$=3.

FIGS. 11A-11D are plots of noise intensities $D_m$ versus P(logic) values (setting γ=50 for the AND gate and γ=36 for the OR gate). Again we have tested that, in this new configuration, the dimensionless time interval [0, 7000] is long enough to let the system switch from the "wrong" to the "correct" well; the simulations in this case follow the same method explained with respect to additive noise. Comparing the results in FIGS. 11A-11D with those in FIG. 7, we see, clearly, the large increment in the optimal window of noise where P(logic)~1, the estimated range is $D_m$=[2.7, 3.5]. This is due to the potential shape that changes with $D_m$ for the multiplicative noise case: in the range where the performance is around 1, $D_m$ makes the potential function $U_g(x)$ asymmetric in order to better perform the AND or OR gates. The LSR in bacteriophage λ is robustly realized for high noise intensities of $D_m$, because the potential barrier of the "wrong" well assumes larger values than in the additive-noise-only case. The different plots in FIGS. 11A-11D show that it is possible to implement LSR also in a broad additive noise intensity range.

In order to simulate the stochastic effects of the gene transcription regulation, we consider the perturbation of the parameter α. As we saw earlier, a is related to the transcription rate, and we set it as α→α+$D_m$η(t) in the presence of a noisy term $D_m$η(t). In this case, Eq. (16) will have the following form for our autoregulatory gene network:

$$\dot{x} = \frac{(\alpha + D_m\eta(t) - 1)x^2 + \sigma_1((\alpha + D_m\eta(t))\beta - 1)x^4 - \sigma_1\sigma_2 x^6}{(\tau + x)(1 + x^2 + \sigma_1 x^4 + \sigma_1\sigma_2 x^6)} + \quad (26)$$

$$\frac{1 - \gamma x - \gamma_y x^2}{\tau + x} + D_n\xi(t) = \frac{(\alpha - 1)x^2 + \sigma_1(\alpha\beta - 1)x^4 - \sigma_1\sigma_2 x^6}{(\tau + x)(1 + x^2 + \sigma_1 x^4 + \sigma_1\sigma_2 x^6)} +$$

$$\frac{1 - \gamma x - \gamma_y x^2}{\tau + x} + \frac{D_m\eta(t)(x^2 + \sigma_1\beta x^4)}{(\tau + x)(1 + x^2 + \sigma_1 x^4 + \sigma_1\sigma_2 x^6)} + D_n\xi(t)$$

where $f(x)$ is the same as in Eq. (19), while h(x) is $$h(x) = \frac{x^2 + \sigma_1\beta x^4}{(\tau + x)(1 + x^2 + \sigma_1 x^4 + \sigma_1\sigma_2 x^6)} \quad (27)$$

For a given α value, the steady-state probability distribution P(x, t) can be obtained by transforming Eq. (26) into a nonlinear Fokker-Planck equation, where x is the protein concentration. Setting Eq. (21) equal to zero, we obtain the longtime probability density function:

$$P_s(x) = N_{mul\_\alpha}\exp(-U_a(x)) \quad (28)$$

where $N_{mul\_\alpha}$ is a normalization term, while the potential $U_a(x)$ takes the form:

$$U_a(x) = -2\int^x \frac{a(y)}{b(y)} + \ln b(x) \quad (29)$$

Because we are dealing with a noisy α value, the terms a(x) and b(x) will have the form:

$$a(x) = f(x) + \frac{1}{4}\frac{\partial}{\partial x}b(x) = f(x) + \frac{1}{4}\frac{\partial}{\partial x}(D_m h(x)^2 + D_n) \quad (30)$$

$$= \frac{(\alpha - 1)x^2 + \sigma_1(\alpha\beta - 1)x^4 - \sigma_1\sigma_2 x^6}{(\tau + x)(1 + x^2 + \sigma_1 x^4 + \sigma_1\sigma_2 x^6)} + \frac{1 - \gamma x - \gamma_y x^2}{\tau + x} +$$

$$\frac{1}{4}\frac{\partial}{\partial x}\left(D_m\left(\frac{x^2 + \sigma_1\beta x^4}{(\tau + x)(1 + x^2 + \sigma_1 x^4 + \sigma_1\sigma_2 x^6)}\right)^2 + D_n\right)$$

and $$b(x) = D_m\left(\frac{x^2 + \sigma_1\beta x^4}{(\tau + x)(1 + x^2 + \sigma_1 x^4 + \sigma_1\sigma_2 x^6)}\right)^2 + D_n \quad (31)$$

Before plotting the performance of LSR, we exhaustively searched for the best α and γ values that can realize the AND and OR gates, for this particular noisy condition.

Figure 12A:
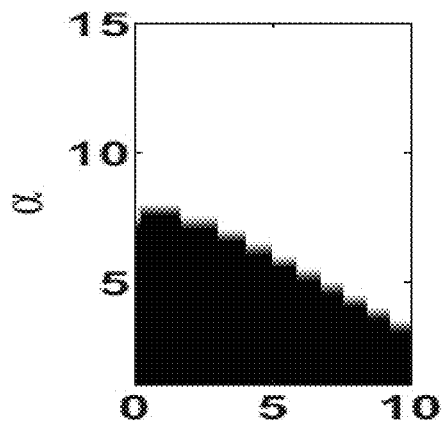
FIGS. 12A-12C are bifurcation diagrams.
Figure 12B:
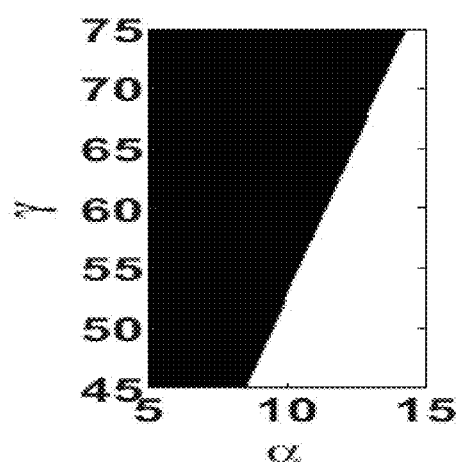
Figure 12C:
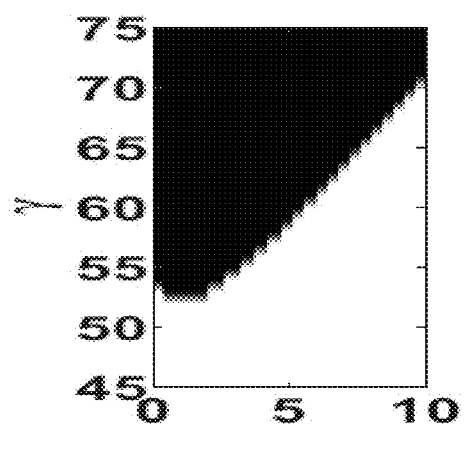

FIGS. 12A-12C are bifurcation diagrams showing parameter ranges where it is possible to well perform the new version of the LSR paradigm (i.e., α→α+$D_m\eta(t)$). In FIG. 12A, we varied $D_m$, and α, and fixed γ=40. In FIG. 12B, we varied α and γ, fixing $D_m$=2. In FIG. 12C we varied $D_m$ and γ, fixing α=10. The black area represents the bistable region, while the white area represents the monostable region. The obtained best values are α=20, 42.4, and 64.8 (for the input sets), and γ=122, 71 to implement the AND and OR gates.

Figure 13A:
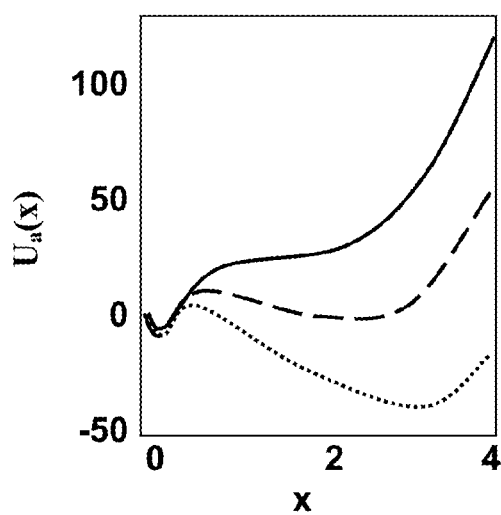
FIGS. 13A-13B are plots of the potential function $U_a(x)$.
Figure 13B:
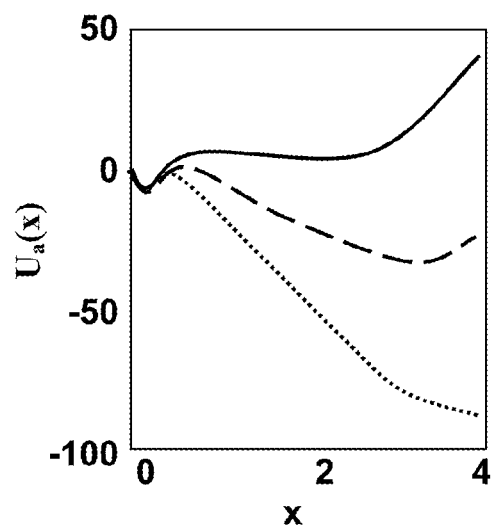

FIGS. 13A-13B are plots of the potential functions $U_a(x)$ for different data inputs for the AND gate (FIG. 13A) and the OR gate (FIG. 13B), using the modified version of LSR paradigm. The solid curve represents the (0,0) case, the long-dashed curve represents the (0,1)/(1,0) cases, and the dotted curve is for (1,1) case. In this case the fixed multiplicative noise intensity is $D_m$=1. It is possible to notice how the left well is always smaller than the right well.

FIGS. 14A and 14B are performance graphs showing the performance of the logic gates OR (the straight line in each panel) and AND (the dashed line in each panel) using the modified LSR paradigm versus the multipicative noise intensity $D_m$, for different $D_n$ values. The consequence of the behavior shown in FIGS. 13A and 13B is evident in the performance graphs shown in FIGS. 14A-14B: P(OR)~1 in a larger range respect P(AND). It means that the possibility to implement a reliable logic gate in a large interval, mostly depend on the possibility to realize an AND gate in presence of noise. In FIGS. 14A-14B, the AND and OR performances are plotted versus the noise intensity $D_m$. Again we have tested that, in this new configuration, the dimensionless time interval [0,7000] is long enough to let the system reach the correct well. The procedure for this case has been repeated 500 times. Differently from the findings related to noise in the degradation rate, we found a difficulty in performing the two logic gate with P(logic)~1 for a large range of $D_m$ (in this case P(logic)~1 for $D_m$=[0.75, 0.95] and $D_n$=1). This is due to the high nonlinearity of the h(x) term in Eq. (27) that has resulted in a new bistable potential. Moreover, simulations with $D_n$~0.5 were not showing a P(logic)~1: this additive noise intensity was not enough to let the system reach the correct well. It is mainly due to the potential function: it considerably changes over the multiplicative noise increment. Following these results, we simulated the performance for different and fixed $D_n$ values, and found that the logic gate performance was improving in presence of a higher additive noise intensity: $D_n$~1 (see FIGS. 14A-14B). The reported values are still in a realistic biological range. The LSR in bacteriophage λ is robustly realized for noise intensities of $D_m$ lower than the previous case related to noise in the degradation rate: the change in the multiplicative noise intensity has a great influence in the shape of the potential function.

Any complete analysis of the dynamics of a nanoscale system needs to take into account the effects of random fluctuations (noise). Moreover, in the context of nonlinear systems, such a description must characterize the delicate interplay between noise and nonlinearity. Instead of being an undesirable and unpredictable term in the dynamics, noise can be a fundamental element. In many natural systems the noise is, actually, the "signal" and not just a laboratory curiosity. In an optimal range of noise intensity values, the performance of a nonlinear system may be optimized and its output is the logical combination of the two input signals. LSR has been introduced as a new direction to implement morphable and reliable logic gates. The main feature of LSR is the capability of the nonlinear device to work in a range of environmental noise; hence, LSR is a practical and reasonable answer for computational devices wherein the noise-floor cannot be suppressed.

Method 10 may utilize "conventional" LSR, and/or a modified version that yields far better performance, in a GRN. A GRN can be visualized as composed of subsets of simpler components (modules), interconnected through input and output signals (analogous to electrical circuits). In the same way that electrical engineers construct circuits, genetic network engineers make use of the biological equivalents of inverters and transistors to manipulate living organisms by connecting these modules into GRNs that can control cellular functions. In the years to come, it can be anticipated that artificial gene networks will become more sophisticated involving, e.g., many interconnected modules or single modules with a wide range of behaviors. LSR affords intriguing possibilities in the realization of engineered genetic networks, specifically biological logic gates in which the actual function of the gate can be changed after the GRN has been assembled: this allows a single module to be used for many different applications via adjusting the network parameters to obtain specific functionalities. We are thus, led to study the realization of a biological logic gate with the demand of being as flexible as possible. As explained in this work, with LSR we can define a large range of values to be adjusted in order to switch from the AND to the OR gate and to be robust to noise. In other words, we are proposing a synthesized GRN that performs the logic functions (e.g. AND/OR) and can be used in different environments and can change its behavior after it has been engineered. In one embodiment, method 10 adapts the LSR paradigm to the bacteriophage λ.

Consider, first, a deterministic model describing the temporal evolution of the concentration of protein in a single-gene network from bacteriophage λ. Bacteria and their temperate phages, like *Escherichia Coli* (E. *Coli*) and λ, exist in symbiotic relationships. After the virus λ infects the bacteria, its evolution proceeds down one of two pathways: lytic (wherein the λ replicates its DNA autonomously, assembles virions and lyses the host) and lysogenic (wherein the phage DNA is incorporated into the host genome). Hence, the bacteriophage λ GRN displays bistability in the choice of one of the two pathways with the characteristics of its stable attractors adjustable by changing the system parameters. Following this, LSR uses the data inputs to adjust the (relative) depths of the two (stable) wells of the potential energy function so that the well representing the desired output (as defined by truth tables) of the computation becomes deeper than the other well. In the bacteriophage λ GRN the two main (adjustable) parameters to implement LSR are α (related to the basal rate of production of the repressor CI), and γ (proportional to the degradation rate of CI). Hence, the logic inputs sets ((0,0), (0,1)/(1,0), and (1,1)) are encoded via α, and control inputs representing the type of computation (AND or OR gates), are encoded through γ.

This leads us to a reconfigurable GRN based logic device, whose workings are underpinned by the interplay between its (intrinsic) nonlinearity and the noise. The output of the computation can be decoded from the final state of the dynamical system; this is 0 or 1 depending on the potential well that the system settles into. In particular this model describes the regulation of the promoter $P_{RM}$ activity in the operator region of the λ phage. Our system is a DNA plasmid consisting of a promoter region and components (of the cI gene) necessary for transcription, translation, and degradation. Bi-stability is reached in the system only when a correct mutual relation between the production and the degradation of protein is realized. Operatively, the dynamics can be adjusted in several ways, e.g. the degradation term changes according to temperature changes, the bacteriophage λ also responds to UV light or, while controlled by the lac repressor in E. *Coli*, the λ repressor amount increases by increasing the inducer amount. The biochemical reactions that control λ phage are very well characterized. They are, naturally, divided into fast and slow categories (see Table III below).

TABLE III

| Fast Reactions | Slow Reactions |
|---|---|
| $2X \rightleftharpoons X_2$ | $D_1 + P \rightarrow D_1 + P + nX$ |
| $D + X_2 \rightleftharpoons D_1$ | $D_2D_1 + P \rightarrow D_2D_1 + P + nX$ |
| $D_1 + X_2 \rightleftharpoons D_2D_1$ | $X \rightarrow \gamma$ |
| $D_2D_1 + X_2 \rightleftharpoons D_3D_2D_1$ | |

X, X2, and D denote the repressor, the repressor dimer, and the DNA promoter site, respectively; $D_i$ denotes dimer binding to the $O_{Ri}$ site, and in order, each fast reaction is characterized by a rate constant: $K_1$, $K_2$, $K_3 = \sigma_1 K_2$, and $K_4 = \sigma_2 K_2$. The variables $\sigma_1$ and $\sigma_2$ represent the binding strengths relative to the dimer-$O_{R1}$ strength. Slow reactions are the transcription and the degradation: P denotes the concentration of RNA polymerase, n is the number of repressor proteins per mRNA transcript. The dimer occupation of $O_{R2}$ enhances the transcription rate of a factor β>1 and it appears only in the second slow biochemical reaction. In the slow reactions the transcription rate is defined as $k_t$, while for degradation, the rate is $k_x$.

Then, defining the concentrations of network components as dynamical variables, $x=[X]$, $x_2=[X_2]$, $d_0=[D]$, $d_1=[D_1]$, $d_2=[D_2D_1]$, and $d_3=[D_3D_2D_1]$, it is possible to write the evolution of the concentration repressor CI as:

$$\dot{x} = -2k_1 + 2k_{-1} + nk_t p_0(d_1 + d_2) - k_x x + r \quad (32)$$

where the concentration of RNA polymerase, $p_0$, is assumed to remain constant during time, r is the basal production rate of the repressor CI, and $K_i = k_i/k_{-1}$ are equilibrium rate constants. Introducing the fast and slow dynamics from Table III one obtains, following a timescale separation argument:

$$\dot{x} = nk_t p_0 d_0 (K_1 K_2 x^2 + \beta \sigma_1 (K_1 K_2)^2 x^4) - k_x x + r = \quad (33)$$

$$\frac{nk_t p_0 d_T (K_1 K_2 x^2 + \beta \sigma_1 (K_1 K_2)^2 x^4)}{1 + K_1 K_2 x^2 + \sigma_1 (K_1 K_2)^2 x^4 + \sigma_1 \sigma_2 (K_1 K_2)^2 x^4 + \sigma_1 \sigma_2 (K_1 K_2)^3 x^6} - k_x x + r$$

Without loss of generality, two of the parameters of Eq. (33) may be eliminated by rescaling the repressor concentration x and the time t. We can define the dimensionless variables $$\tilde{x} = x\sqrt{K_1 K_2}$$

and $$\tilde{t} = t\sqrt{K_1 K_2}\, r.$$

The final equation has the form (we have suppressed the overbar on x):

$$\dot{x} = \frac{\alpha(2x^2 + 50x^4)}{25 + 29x^2 + 52x^4 + 4x^6)} - \gamma x + 1 + D_n \xi(t) \quad (34)$$

where we introduce the dimensionless parameters $$\alpha = nk_t p_0 d_T / r, \gamma = k_x / (\sqrt{K_1 K_2}\, r)$$

and we have also added a noise term representing fluctuations affecting the system.

Note that, in the absence of the noise $\xi(t)$ (discussed below), the dimensionless Eq. (34), can be mapped onto actual biological dynamics via the appropriate choice of parameters; in particular, we set (and retain throughout this work) the degree of transcriptional activation as $\beta=11$, the equilibrium constant for cI dimerization as $K_1=0.05\, nM^{-1}$, the equilibrium constant for cI $-O_R$ reaction as $K_2=0.33\, nM^{-1}$, the binding affinity for cI dimer to $O_{R2}$ relative to $O_{R1}$ as $\sigma_1=2$, and the binding affinity for cI dimer to $O_{R3}$ relative to $O_{R1}$ as $\sigma_2=0.08$ to maintain the connection to biologically accessible parameter ranges. Random fluctuations arise in these systems in several ways. For example, any cellular component that is affected by noise can act as an extrinsic random source for other systems with which interactions occur. Here, we focus on the (additive) external noise that can stem from random variations in the (external) control parameters. $\xi(t)$ is zero-mean Gaussian noise ($<\xi(t)>=0$), and we assume that random fluctuations have correlation time scale smaller than any other reaction time scale in the system, so that the noise can be taken to be delta correlated, i.e., $<\xi(t)\xi(t')>=\delta(t-t')$, with $D_n$ being the measure of the noise intensity. Equation (34) is the core of the computing model.

Figure 15A:
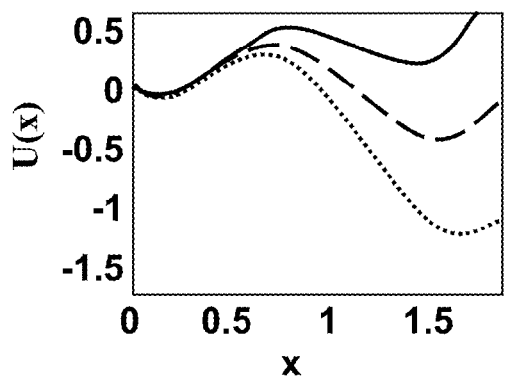
FIGS. 15A-15D are plots of potential functions.
Figure 15B:
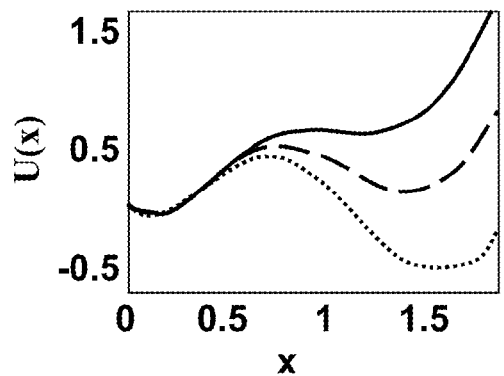
Figure 15C:
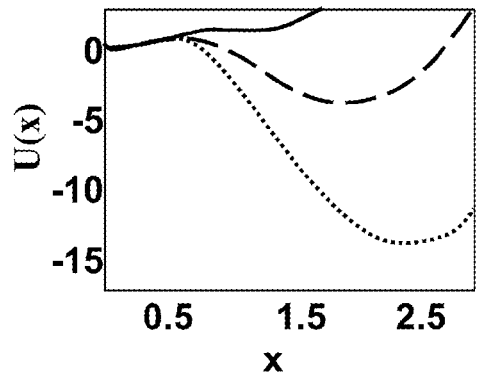
Figure 15D:
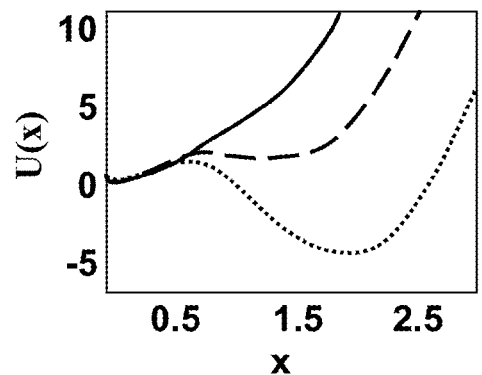

FIGS. 15A-15D are plots of potential functions for different data inputs for the OR gate (FIG. 15A) and the AND gate (FIG. 15B) using the "conventional" LSR paradigm, and for the OR gate (FIG. 15C) and the AND gate (FIG. 15D) using the modified LSR paradigm. The solid curve represents the (0,0) case, the long-dashed curve represents the (0,1)/(1,0) cases, and the dotted curve is for (1,1) case. Values were chosen in the accessible parameter range, related to the most robust configuration. FIGS. 15A-15B: $\alpha=15$, 16.5, 18, and $\gamma=8.0$ (AND), $\gamma=7.5$ (OR). FIGS. 15C-15D: $\alpha=20, 31, 42$, and $\gamma=15.0$ (AND), $\gamma=11.0$ (OR).

The potential function $U(x)$, of the system (deterministic, i.e. with $\xi(t)=0$) in Eq. 34, is obtained, analytically, by integrating the right hand side of (34), with $\alpha$ and $\gamma$ the two accessible parameters (taken in the regime of bistability). The plotted curves of $U(x)$ shown in FIGS. 15A-15D represent the most robust configuration in the limited range of parameters, $\alpha$ and $\gamma$, germane to the biological system in the bistable configuration. Several simulations have been made to exhaustively search (in the parameter space) the most robust configuration of parameters that yields the best logic gate performances. For the "conventional" LSR paradigm, we obtained (numerically) $\alpha=15$, 16.5, and 18 (respectively for (0, 0), (0, 1)/(1, 0), and (1, 1)), and $\gamma=8$ yields the AND gate and $\gamma=7.5$ the OR gate as the control input for programming the gate.

A fundamental observation is that the desired logical output occurs consistently and robustly only in an optimal range of noise values, in line with the tenets of stochastic resonance. In the absence of a noise floor, this model doesn't work correctly; orbits may be trapped in the wrong well. Increasing the noise intensity beyond its optimal range leads to random switching between wells and the output no longer conforms to the truth tables. To quantify this behavior with respect to noise in this (designed) logic gate, we measured its performance as defined as the ratio of success in realizing the desired gate, over the total number of attempts; this ratio is, also, the probability of realizing the desired gate, and is shown (for OR and AND gates) in FIGS. 16A-16B.

Figure 16A:
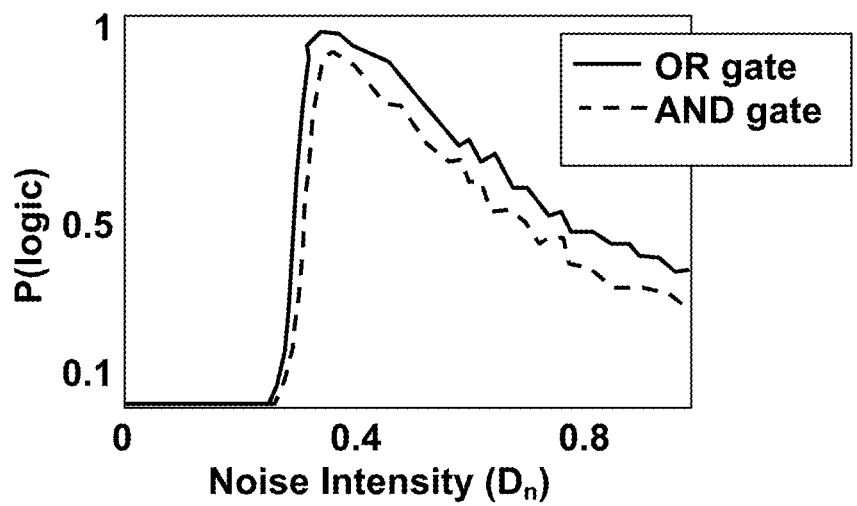
FIGS. 16A-16B are plots representing the performance of logic gates.
Figure 16B:
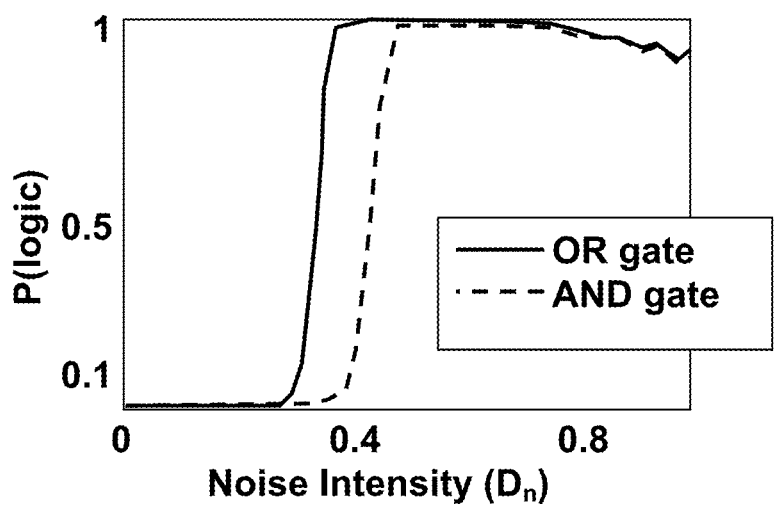

FIGS. 16A-16B are plots representing the performance of logic gates OR and AND using the "conventional" LSR paradigm (FIG. 16A), and the modified paradigm (FIG. 16B). We note, here, that the probabilities in FIG. 16A do not take the value unity. This can be traced back to the structure of the potential function for this GRN model, which is bistable only in a restricted regime of parameter values; hence this particular embodiment does not yield enough dynamic range to successfully implement the LSR paradigm. Moreover, in our performance definition, for each noise value, we have checked the agreement between the simulated logical outputs for all data inputs ((0, 0), (0, 1)/(1, 0), and (1, 1)) and the respective truth table values of the gate under study. If one of the outputs doesn't realize the desired gate, we mark that as a failure. In other words, if for example we consider the plot depicted in FIG. 15A, for each noise value, the least robust potential configuration (among the three plotted) will have the highest influence on the performance quality of this considered gate. Different combinations of parameters have been tried, but unsuccessfully, because of the restricted dynamic range implicit in the model and the biological properties that are endemic to bacteriophage $\lambda$.

This has led us to propose a new version of the LSR principle, via a manipulation of the "conventional" LSR principle, to achieve a bacteriophage $\lambda$ configuration that is still biologically correct. As detailed above, the LSR paradigm works in the range of $\alpha$ and $\gamma$ parameters that induce bistability, and for all the distinct logic input sets (0,0), (0,1), (1,0) and (1,1). To "adjust" the bacteriophage $\lambda$ to conform to the LSR paradigm implies limiting the parameter interval to a narrow region. In the improved LSR paradigm, the idea is to encode inputs as parameters of the GRN model so that the undesired well (almost) disappears, and to take advantage of stochastic resonance for the cases where the unwanted well cannot be removed from the potential function, $U(x)$. The second case usually happens when the inputs are (0,1)/(1,0). With this proposed model, we are still working in a parameter interval that is biologically meaningful and we strive to take into account all the range of $\alpha$ values that represent all the possible system configurations, without restricting our study to the bistable region. In other terms, it can happen that the (0,0) or (1,1) cases can be realized when $U(x)$ is monostable as shown in FIG. 1 (solid curve of the FIGS. 15C & 15D).

By "controlling" the second parameter, $\gamma$, we can deepen either well selectively; hence with the appropriate amount of noise, trajectories will switch to the deeper well and remain there. This updated model for computing is, then, underpinned by the (numerically obtained) data inputs $\alpha=20$, 31, and 42. We note that, now, $\gamma=15$ yields the AND gate and $\gamma=11$ the OR gate. All numbers for the $\alpha$ definition and the $\gamma$ values have been obtained through several simulations (as mentioned above). The potential functions for AND and OR gates for different data inputs are presented in FIGS. 15C & 15D with the probability of realizing these gates, using the modified paradigm, shown in FIG. 16B. We note that the two gates are robust to noise in the same range of noise and amenable to the design of a morphable logic gate; in addition, we observe a range of noise intensities for which P(logic)=1. The updated LSR paradigm yields, however, greater robustness to external fluctuations. Finally we note that, to obtain the best performance in the logic gates, two possible solutions can be assessed: the change of noise intensity or the variation of the parameter values, thereby adjusting the system dynamics to an optimal configuration, so that P(logic)~1 as desired; for a nonlinear system this is tantamount (as already noted earlier) to changing the transfer characteristic thereby, in effect, "tuning" the noise.

FIGS. 17A-17B represent the gate performance by plotting noise intensities $D_n$ against α values (while γ=15 for the AND gate (FIG. 17A) and γ=11 for the OR gate (FIG. 17B)). For a fixed value of noise (for example the one mandated by nature) it is possible to select the "best" α value. It is interesting to note that, for our particular choice of model parameters, if noise intensity values are in the [0.5, 0.8] regime, there is a reasonably large range of α values for which P(logic)~1, as desired.

To summarize, we have adapted and implemented LSR on a GRN model, the bacteriophage λ. The resultant computing device is able to work as an AND or OR gate interchangeably in the presence of noise. In a completely analogous way, by setting the output values in the reverse configuration, we can realize NAND and NOR gates in almost the same optimal noise intensity regime as the previous case (e.g. the left well can represent the 1 for output of the NAND/NOR reconfigurable gate, instead of 0 as set previously for the AND/OR gate). Noise is critical for the existence and operation of the gates. We have computed the gate "performance" as a function of noise intensity and shown that the biological system output is the logical combination of the two data inputs for a range of noise intensities, and the GRN phage λ can switch from the AND to OR gate as desired; this switching can be accomplished, for a fixed external noise level, by adjusting other deterministic system parameters. LSR on a GRN, that has the capability of being reconfigured, could be combined, in near future, with other logic modules (done by different sets of input/output signals) to increase the computational power and functionality of an engineered GRN. Such networks may allow predictable and robust control in fluctuating cellular environments and thereby have a significant impact in the design of synthetic biological systems such as recently created bacterial cells controlled by chemically synthesized genomes.

From the above description of the method for providing a biological logic gate, it is manifest that various techniques may be used for implementing the concepts of method 10 without departing from its scope. The described embodiments are to be considered in all respects as illustrative and not restrictive. It should also be understood that method 10 is not limited to the particular embodiments described herein, but is capable of many embodiments without departing from the scope of the claims.

What is claimed is:

1. A method for providing a biological logic gate comprising the following steps:
    subjecting a bistable autoregulatory gene network (GRN) to a noisy background, wherein the noisy background comprises additive noise and multiplicative noise;
    identifying adjustable parameters of the GRN;
    using a modified logical stochastic resonance (LSR) paradigm to determine values of the GRN parameters which result in the GRN performing different logic gate functions, wherein inputs are encoded as parameters of the GRN such that an undesired potential well of a potential function, U(x) nearly disappears and using stochastic resonance for cases where the undesired potential well cannot be removed from the potential function, U(x);
    limiting a parameter interval of the GRN to adjust the GRN to conform to the modified LSR paradigm; and
    setting the parameter values of the GRN such that the GRN is synthesized to perform a first logic gate function.

2. The method of claim 1, further comprising altering the parameter values of the GRN such that the GRN performs a second logic gate function instead of the first logic gate function.

3. The method of claim 2, wherein the first logic gate function is equivalent to an OR logic gate and the second logic gate function is equivalent to an AND logic gate.

4. The method of claim 1, wherein the first logic gate function is equivalent to an AND logic gate.

5. The method of claim 1, wherein the first logic gate function is equivalent to an OR logic gate.

6. The method of claim 1, wherein the first logic gate function is equivalent to a NOR logic gate.

7. The method of claim 1, wherein the first logic gate function is equivalent to a NAND logic gate.

8. The method of claim 1, wherein the GRN is a bacteriophage λ.

9. The method of claim 1, wherein the noisy background comprises biological noise.

10. The method of claim 1, wherein the GRN is characterized by a nonlinear, bistable potential energy function having a first potential well and a second potential well, both wells representing steady states of the GRN.

11. The method of claim 10, further comprising the step of determining that the GRN is experiencing an intensity of noise within a desired range of noise intensity values, wherein the GRN comprises three operator sites that overlap a promoter region and a cI gene sufficient for transcription, translation, and degradation of a cI gene product, wherein the first potential well corresponds to a first set of values of a repressor protein concentration, and the second potential well corresponds to a second set of values of the repressor protein concentration.

12. The method of claim 11 wherein the step of setting the parameter values of the GRN such that the GRN performs a first logic gate function comprises the further steps of:
    applying a tunable control parameter to the GRN to select logic gate functionality, wherein the tunable control parameter is proportional to the degradation rate of a repressor CI;
    adjusting a basal rate of production of the repressor CI as a data input to the GRN, wherein the data input encodes values of a set of logical inputs; and
    detecting a logical output of the GRN by detecting an output state of the GRN by measuring the repressor protein concentration, wherein a measurement being of the first potential well corresponds to the logical output having a first value and the measurement being of the second well corresponds to the logical output having a second value, and wherein the logical output is predictable, given the values of the set of logical inputs, according to a truth table corresponding to the selected logic gate functionality.

\* \* \* \* \*